United States Patent [19]

Pupo et al.

[11] 4,126,461
[45] Nov. 21, 1978

[54] BLACK-AND-WHITE PHOTOGRAPHIC ELEMENTS AND PROCESSES

[75] Inventors: David A. Pupo, Churchville; Samuel J. Ciurca, Jr.; Grant M. Haist, both of Rochester; James R. King, Webster, all of N.Y.

[73] Assignee: Eastman Kodak Company, Rochester, N.Y.

[21] Appl. No.: 806,244

[22] Filed: Jun. 13, 1977

[51] Int. Cl.² .................. G03C 5/26; G03C 1/06; G03C 1/40
[52] U.S. Cl. .................. 96/50 R; 96/60 BF; 96/61 R; 96/76 R; 96/95; 96/100 R
[58] Field of Search .................. 96/22, 50, 74, 95, 67, 96/60 R, 61 R, 55, 100, 60 BF, 76 R

[56] References Cited

U.S. PATENT DOCUMENTS

| | | | |
|---|---|---|---|
| 2,181,944 | 12/1939 | Kleine | 96/100 |
| 2,189,817 | 2/1940 | Morris | 96/55 |
| 2,310,982 | 2/1943 | Meschter | 96/59 |
| 2,333,106 | 11/1943 | Kendall et al. | 96/100 |
| 2,443,909 | 6/1948 | Hanson et al. | 96/12 |
| 3,497,350 | 2/1970 | Yutzy et al. | 96/74 |
| 3,622,629 | 11/1971 | Lugosy | 96/66 |
| 3,674,490 | 7/1972 | Matejec | 96/48 R |
| 3,770,431 | 11/1973 | Gates et al. | 96/3 |
| 3,772,014 | 11/1973 | Scullard | 96/3 |
| 3,929,486 | 12/1975 | Habu et al. | 96/76 R |

FOREIGN PATENT DOCUMENTS 2,644,194  4/1977  Fed. Rep. of Germany.
2,650,764  5/1977  Fed. Rep. of Germany.

*Primary Examiner*—Mary F. Kelley
*Attorney, Agent, or Firm*—J. G. Levitt

[57] ABSTRACT

Photographic elements for providing black-and-white images contain a silver halide emulsion having associated therewith a non-diffusible resorcinol coupler and a color developing agent or a precursor of a color developing agent. The elements can be processed by simple alkaline activation. Since image density is derived at least in part from the resorcinol coupler, lower silver halide coverages can be employed or the silver can be recovered, or both.

37 Claims, No Drawings

BLACK-AND-WHITE PHOTOGRAPHIC ELEMENTS AND PROCESSES

This invention relates to novel photographic elements and processes useful for producing black-and-white photographic images. More particularly, it relates to such elements wherein the image is derived at least in part from a nondiffusible resorcinol coupler.

The vast majority of black-and-white photographic images make use of metallic silver to provide image density. Such an image is typically obtained in a process involving imagewise exposure of a light-sensitive silver salt, most commonly a silver halide, followed by a development step in which the silver salt is selectively reduced to metallic silver to provide the image. Depending upon the particular process, other steps may be employed. However, the common feature of such black-and-white processes is that a silver salt is converted to metallic silver which provides image density. By way of comparison, color photographic elements employing light-sensitive silver salts, such as silver halide, yield an image composed of one or more organic dyes. This permits the recovery and possible reuse of the silver from the photographic elements.

With the growing scarcity of silver, it would be desirable if photographic elements for the production of black-and-white images were available which retain the many desirable features of elements based on photographic silver halides, yet which make use of an organic molecule to provide, at least in part, the image density. Such an element would permit the recovery and possible reuse of the silver, as in the case of color photographic elements. Additionally or alternatively, it would permit the use of smaller quantities of silver halide in the element than would otherwise be required to obtain an image of comparable density.

From time to time it has been observed that some photographic couplers yield black-and-white or neutral density images. Thus, Seymour U.S. Pat. No. 1,939,231, in describing a photographic reversal process for producing images both in color and black-and-white, notes in Example II that a developer solution containing 1,5-dihydroxynaphthalene and 2,5-dibromo-4-aminophenol produces a very nearly neutral image.

Kleine et al U.S. Pat. No. 2,181,944 describes silver halide emulsions containing a dyestuff former which can be converted into a "black dyestuff." These dyestuff formers are described as compounds in which "the coupling group is linked to a polynuclear radical" or as compounds which have been obtained by "linking several dyestuff components which individually form colors by color-forming development" so that the combination of the various colors yields a neutral.

Meschter U.S. Pat. No. 2,310,982 is directed to a reversal process for the production of black-and-white images in which a developer solution containing an arylene diamino photographic developing agent and a nitrogenous base is employed with presumably known black color-formers.

Kendall et al U.S. Pat. No. 2,333,106 relates to certain 4-hydroxypyrazole color-formers which are said to yield gray, blue-gray, and blue images that are useful in the production of photographic dyestuff images in neutral tones.

These older processes have suffered from one or more disadvantages which militated against their use. Thus, some did not live up to expectations in providing truly neutral images, but resulted in images of non-neutral shades. Others yielded images of poor dye density or images which were unstable on keeping. Yet others employed expensive and different to prepare color-formers. Some of these disadvantages are discussed in Lugosy U.S. Pat. No. 3,622,629 which similarly is directed to the production of black-and-white images in which image density is provided by an organic dyestuff.

Lugosy U.S. Pat. No. 3,622,629 makes use of a "developer-coupler" in which a p-aminophenol nucleus is linked to a dye-forming nucleus. These developer-coupler compounds are said to yield black dyes. They can be incorporated in developer solutions or they can be incorporated directly in photographic elements. However, the presence in a photographic element of a compound which by its very nature contains a dye-former moiety in intimate proximity to a moiety which will react with that dye-former to yield a dye (i.e. a p-aminophenol developer moiety) is likely to lead to materials which have poor storage stability and which yield images that form stain in background areas on keeping.

Thus, there remains a need for black-and-white photographic materials which are stable on storage and which yield black-and-white images having good keeping properties. Preferably, such materials should be rapidly developable by treatment with simple solutions and should require a minimum of processing steps to yield an image of good stability.

We have found silver halide photographic elements containing non-diffusible resorcinol couplers and incorporated developing agents in which the resorcinol coupler provides a dye image which can enhance the silver image or replace the silver image. These elements can be simply processed by alkaline activation to give very stable dye images having extremely broad spectral absorption with no sharp peaks in the visible region of the spectrum. Proper selection of the non-diffusible resorcinol coupler and the developing agent gives neutral dye images. Since these compositions are useful to enhance or replace metallic silver density, they permit the use of lower amounts of silver halide than would otherwise be required to obtain images of equal density or the recovery of all of the metallic silver from the element or both.

Resorcinol and derivatives of resorcinol have been disclosed previously for use in photographic elements and processes.

British Pat. No. 1,205,824 describes the use of resorcinol and various resorcinol derivatives in what is described as an anti-fogging composition which is applied to a color photographic element during photographic processing between the pre-hardening step and the first development step. Treatment with this antifogging composition is said to prevent the formation of development fog and to increase dye density in the color image.

Habu et al U.S. Pat. No. 3,929,486 describes the incorporation in photographic elements of resorcinol derivatives, together with other addenda, to reduce the propensity of the elements to form fog.

In Morris et al U.S. Pat. No. 2,189,817 certain ethers of resorcinol are used as color couplers, yielding on color development typically blue-colored images.

Resorcinol compounds have also been used as scavengers which react with oxidized color developing agents to yield soluble or colorless reaction products. Hanson et al U.S. Pat. No. 2,443,909, Salminen U.S. Pat. No. 2,742,832, Gates et al U.S. Pat. No. 3,770,431 and Scullard U.S. Pat. No. 3,772,014 are examples of such disclosures. The last two patents, i.e. Gates et al. and Scullard, describe as scavengers in diffusion transfer elements resorcinol compounds some of which are the same as resorcinol compounds employed in the present invention. However, these two patents do not recognize or suggest the black-and-white photographic elements of the present invention or the fact that useful neutral density dye images could be obtained with such resorcinol compounds.

In accordance with one aspect of this invention there is provided a black-and-white photographic element comprising a support bearing a photographic silver halide emulsion, a non-diffusible resorcinol coupler and a color developing agent or a precursor of a color developing agent, the element yielding, upon exposure and development to a density of between 0.3 and 2.0, a spectrophotometric curve in which the density of any 10 nm interval in the range of 420 to 650 nm does not depart by more than 10 percent from the mean density over that range.

Such elements, after imagewise exposure, can be rapidly developed to yield a visible image merely by treatment with an alkaline activator solution so as to raise the pH in the element to a lever which 1) will cause conversion of the color developer agent precursor, if one is employed, to a color developing agent, and 2) will be conducive to a) the imagewise reduction of silver halide by the color developing agent and b) the coupling of imagewise oxidized color developing agent and the non-diffusible resorcinol coupler to yield dye.

Thus, in accordance with another aspect of this invention there is provided a process of providing a black-and-white image in an exposed photographic element comprising a support bearing a photographic silver halide emulsion, a non-diffusible resorcinol coupler and a color developing agent or a precursor of a color developing agent, the process comprising activating the element by contacting it with an aqueous alkaline solution to develop a neutral density image as a function of exposure.

Alkaline activation can be the only processing step if the coverage of silver halide in the element is sufficiently low as to not give rise to appreciable background print-out upon keeping or if only a temporary image is required. Otherwise, it is desirable to remove undeveloped silver halide from the element by a fixing step and in some instances it may be desirable to remove the developed silver by a bleach step. Where a bleach step is employed, it optionally can be combined with the fixing step, by employing a bleach-fix bath.

The non-diffusible resorcinol couplers when incorporated in elements of the present invention lead to black-and-white images typically having a neutral hue. However, in some instances non-neutral or colored images may be obtained, depending upon the particular combination of nondiffusible resorcinol coupler and color developing agent or color developing agent precursor, the nature of other components in the composition and the composition of the alkaline activator. Such images share with neutral images the advantages of the present invention such as stability and ease of development and are useful where a colored or non-neutral image is desired or is not objectionable for the intended use of the image.

The term "non-diffusible" as used herein has the meaning commonly applied to that term in photography and denotes materials that for all practical purposes do not migrate or wander through layers of organic colloid, such as gelatin, when incorporated in photographic elements. With certain alkaline activator solutions containing highly active solvents a minor proportion of the coupler may diffuse into the activator solution. This loss of coupler does not have a significant adverse effect on either image density or image sharpness and the couplers are considered non-diffusible.

Included within the term neutral are hues which occasionally are referred to as blue-black, gray, purple-black, etc. Whether or not a given image is neutral can be rapidly determined by visual inspection. A more precise procedure for determining whether or not an image is neutral would be to formulate an element and then expose and develop it by alkaline activation to yield a density of between 0.3 and 2.0. Alkaline activation would typically be with one of the alkaline activators described hereinafter intended to be used with the element to provide an image, and could be followed by others of the processing steps described. This density would then be employed to generate a spectrophotometric curve of wavelength versus diffuse reflection density or diffuse transmission density (depending upon whether the support is opaque or transparent), using commonly available equipment, such as a General Electric Recording Spectrophotometer or a Diana Hardy Spectrophotometer. If the spectrophotometric plot of density versus wavelength does not contain any 10 nm interval in the range of 420 to 650 nm which departs by more than 10 percent from the mean density over that range, then the image obtained would be considered to have a neutral hue for the purpose of this invention.

Additional improvements in such properties of the photographic element as storage stability and dye yield can be obtained by incorporating in the element such components as a metal salt stabilizer for the color developing agent or its precursor, an electron transfer agent, and a latex. The element can additionally contain such components as hardeners, buffering agents, coating aids, and the like.

Non-diffusible resorcinol couplers which are useful in the practice of the present invention can be represented by the following structural formula:

COUP–LINK–BALL where COUP is a 2,6-dihydroxyphenyl moiety, a 2,4-dihydroxyphenyl moiety or a 3,5-dihydroxyphenyl moiety, LINK is a divalent linking group which serves to join the COUP moiety to the BALL moiety and BALL is a moiety of such size and configuration as to confer on the coupler sufficient bulk to prevent it, and the resultant dye, from diffusing or wandering from the layer in which it is coated.

The COUP moiety is preferably unsubstituted in its remaining ring positions, although it can contain non-bulky, relatively low molecular weight substituents in one or more of the remaining positions on the benzene ring. Typical of such optional substituents are lower alkyl groups of 1 to 4 carbon atoms such as methyl, ethyl, propyl and butyl, and halogen substituents, such as chloro and bromo.

The LINK group can be any divalent group which will serve to connect the COUP moiety with the BALL moiety. As indicated previously, the particular structure of the coupler will affect the hue of the resultant dye image, and accordingly certain LINK groups are preferred over others since they yield neutral dye images more consistently. Such preferred LINK groups are:

—NHCO—,
—CONH—,
—NHCONH—,
—NHSO$_2$—,
—NH— and
—COO—;

wherein the lefthand bond of the LINK group, as shown above, is directly joined to the COUP moiety and the righthand bond is directly joined to the BALL moiety.

The BALL moiety can be any group which will confer on the coupler molecule sufficient bulk so as to prevent it from migrating or wandering from the location in the element in which it is incorporated. Numerous such moieties are known for use in connection with couplers intended for incorporation in photographic elements and can be employed in the non-diffusible resorcinol couplers employed in this invention. As in the case of the LINK group, certain BALL moieties are preferred since non-diffusible resorcinol couplers containing them have been found to give neutral density dye images more consistently. Accordingly, preferred BALL groups include:

(a) phenyl and naphthyl groups which may be unsubstituted or substituted with such groups as:
   hydroxy,
   halo, such as chloro, bromo and iodo,
   sulfonyl halide,
   nitro,
   cyano,
   amino,
   alkyl of 1 to 20 carbon atoms, including substituted alkyl (such as haloalkyl),
   alkoxy of 1 to 20 carbon atoms,
   alkylthio of 1 to 20 carbon atoms, and
   alkoxycarbonyl of 2 to 21 carbon atoms;

(b) alkyl groups of 3 to 20 carbon atoms; and (c) heterocyclic groups containing a ring system of 5 to 10 nuclear atoms, and containing hetero atoms such as oxygen, nitrogen and sulfur, e.g., furyl, quinolyl, thienyl, etc. The BALL moiety can also be a polymeric moiety, or it can be one of the above BALL moieties to which is attached a second COUP-LINK- group so as to form a bis-compound symmetrical or unsymmetrical around the BALL moiety. Non-diffusibility of the resorcinol couplers is enhanced when the alkyl, alkoxy, alkylthio and alkoxycarbonyl groups which comprise the BALL moiety contain 8 or more carbon atoms, e.g. 8 to 20 carbon atoms.

Preferred non-diffusible resorcinol couplers useful in the elements of this invention can be represented by the following structural formula:

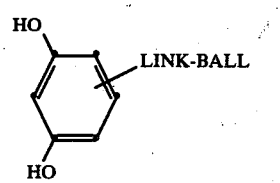

wherein
LINK and BALL are the preferred such groups defined immediately above.

Particularly preferred are those non-diffusible resorcinol couplers having the above structural formula wherein LINK is a —NHCO— group or a —COO— group, and BALL is an alkyl group of 3 to 20 carbon atoms or a phenyl group substituted with an alkyl group of 1 to 20 carbon atoms or with an alkoxy group of 1 to 20 carbon atoms. Also particularly preferred are those non-diffusible resorcinol couplers in which the —LINK-BALL moiety is attached to the COUP moiety so that the COUP moiety is a 2,6-dihydroxyphenyl moiety; i.e., —LINK-BALL is ortho to each hydroxy group in COUP.

Representative couplers which are useful in the practice of the invention are:

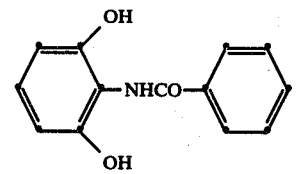
RC-1

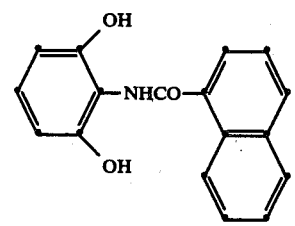
RC-2

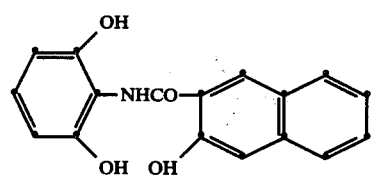
RC-3

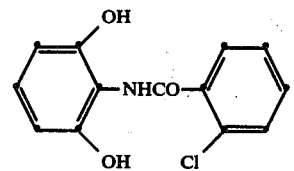
RC-4

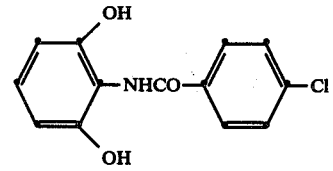
RC-5

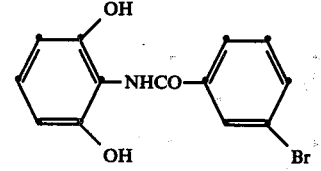
RC-6

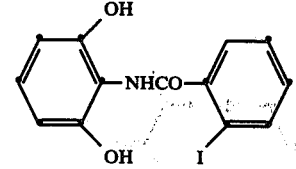
RC-7

-continued
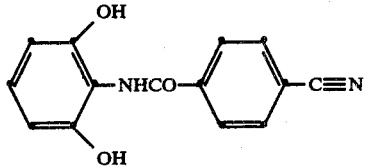 RC-8
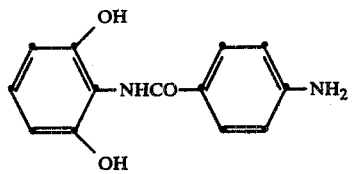 RC-9
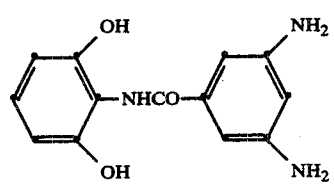 RC-10
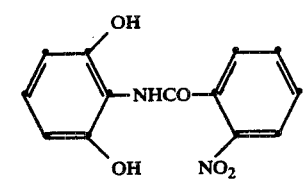 RC-11
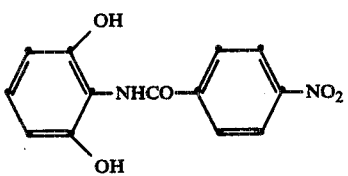 RC-12
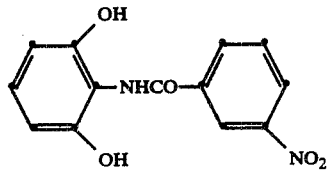 RC-13
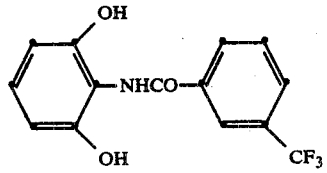 RC-14
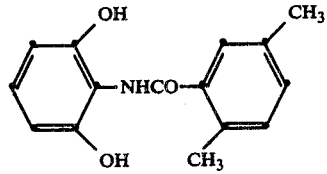 RC-15
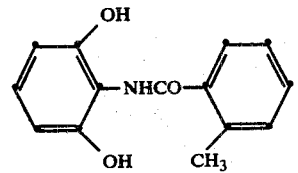 RC-16
-continued
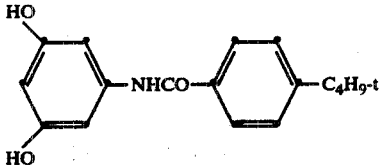 RC-17
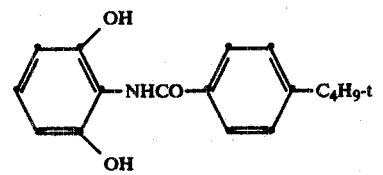 RC-18
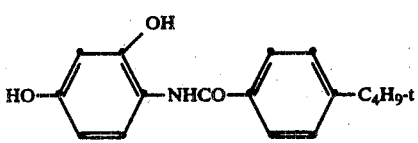 RC-19
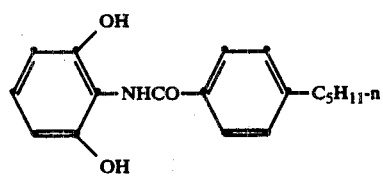 RC-20
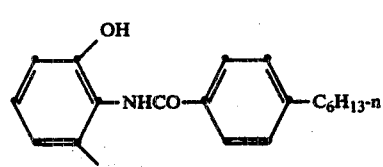 RC-21
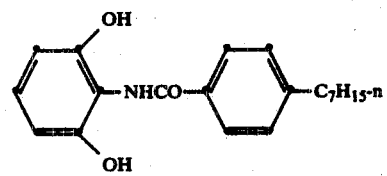 RC-22
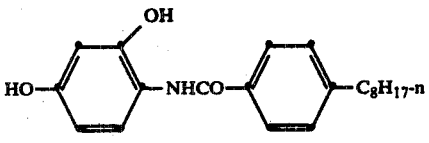 RC-23
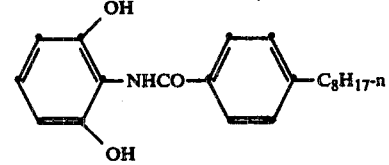 RC-24
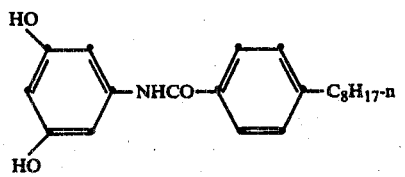 RC-25

-continued
RC-26 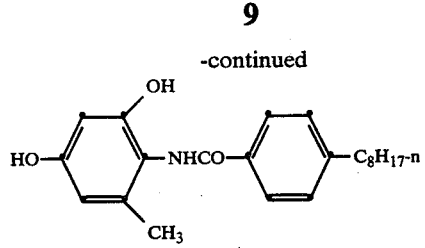
RC-27 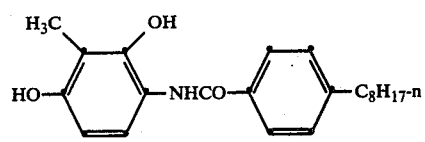
RC-28 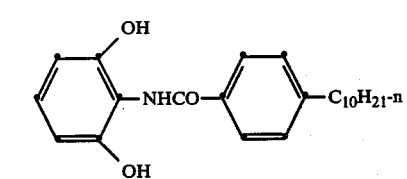
RC-29 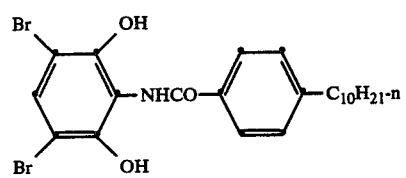
RC-30 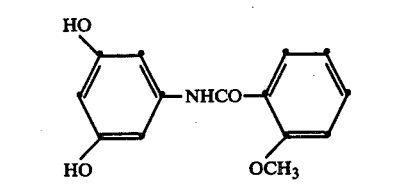
RC-31 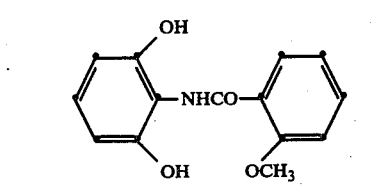
RC-32 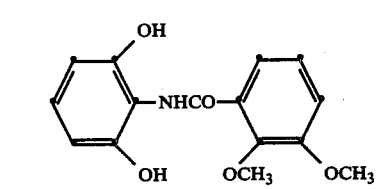
RC-33 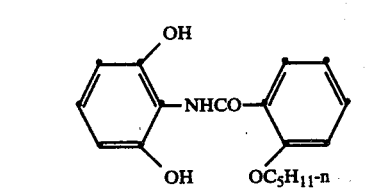
RC-34 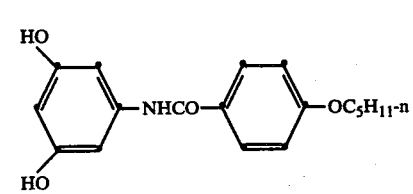
-continued
RC-35 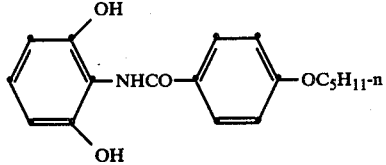
RC-36 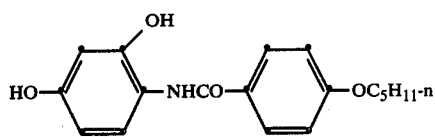
RC-37 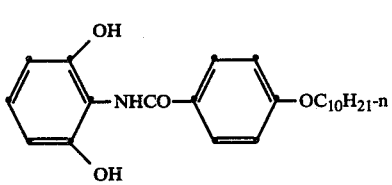
RC-38 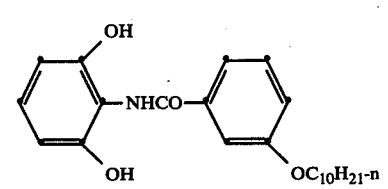
RC-39 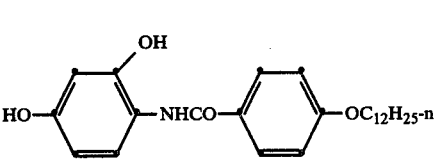
RC-40 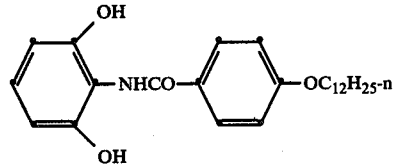
RC-41 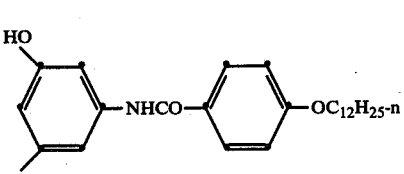
RC-42 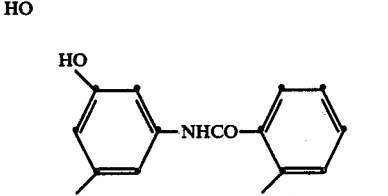
RC-43 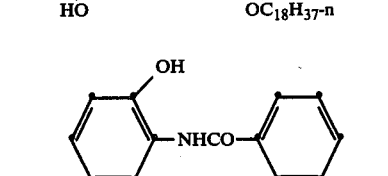

RC-44 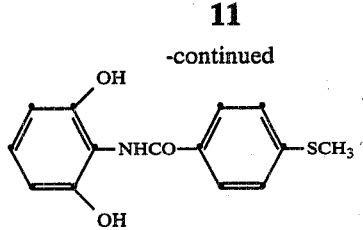
RC-45 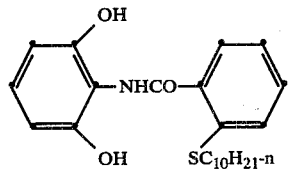
RC-46 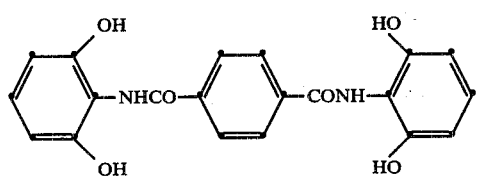
RC-47 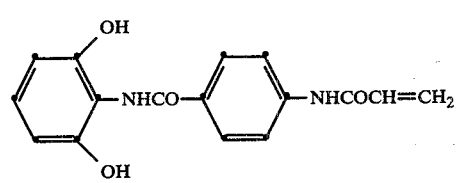
RC-48 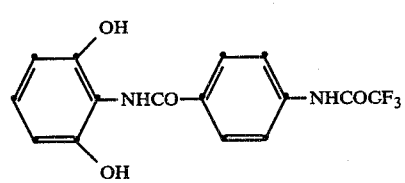
RC-49 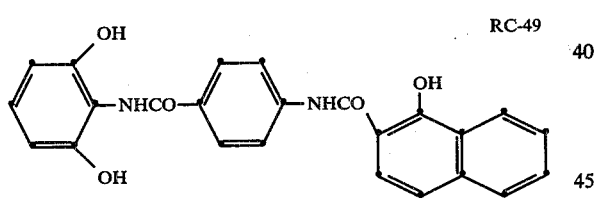
RC-50 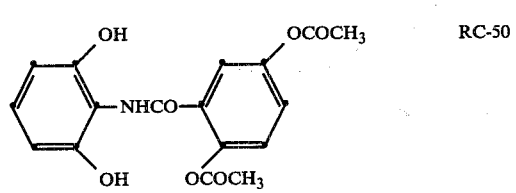
RC-51 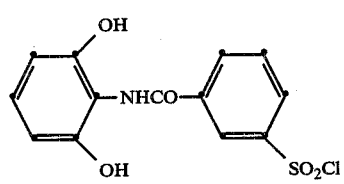
RC-52 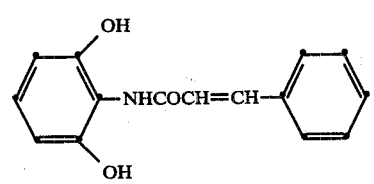
RC-53 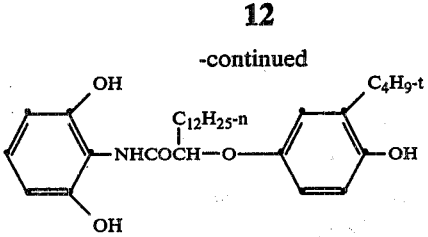
RC-54 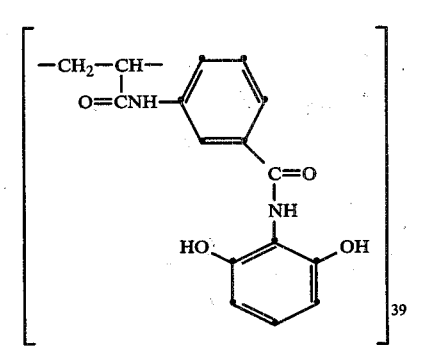
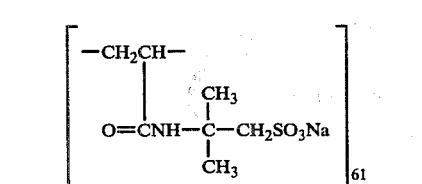
RC-55 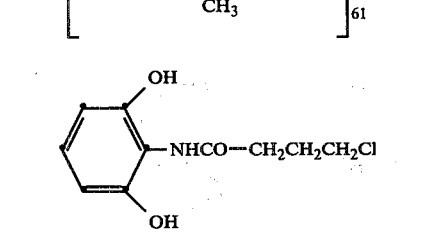
RC-56 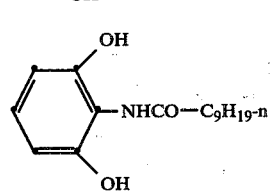
RC-57 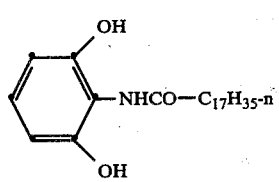
RC-58 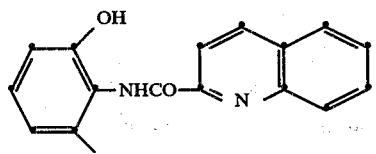
RC-59 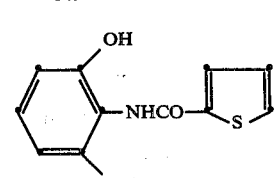

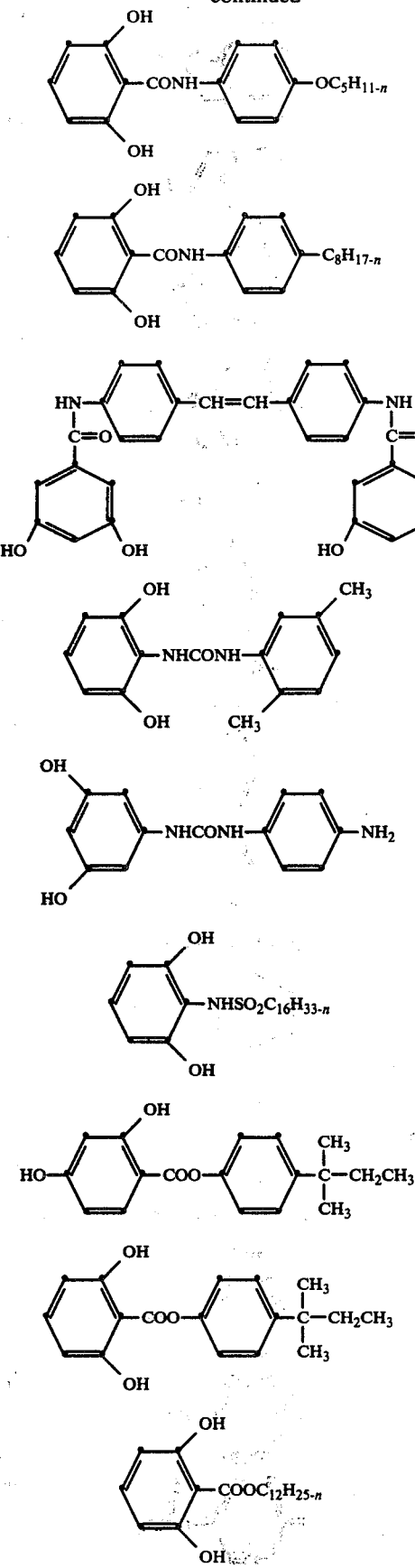

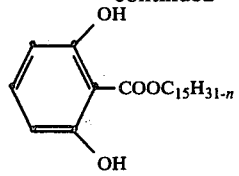

Resorcinol couplers employed in this invention can be prepared from aminoresorcinols or dihydroxybenzoic acids. For some of the resorcinol couplers, an appropriate amino-resorcinol can be condensed with an appropriate acid chloride in the presence of a base (such as pyridine, quinoline, N,N-dimethylaniline, etc.), as an acid acceptor to yield the desired resorcinol coupler. Other resorcinol couplers can be prepared by condensation of an appropriate dihydroxy benzoic acid with an appropriate amine in the presence of a phosphorous trichloride catalyst and an amine acid acceptor. These same resorcinol couplers can be prepared by first converting the dihydroxybenzoic acid to the acid chloride, (while blocking the hydroxyl groups to prevent the acid chloride from reacting with itself) and then condensing the resultant acid chloride with an appropriate amine, followed by hydrolysis to deblock the hydroxy groups. Yet other resorcinol couplers can be prepared by converting an appropriate dihydroxybenzoic acid to its methyl ester and then conducting a transesterification reaction with an appropriate alcohol in the presence of a base catalyst, such as tetraisopropyl orthotitanate. These same resorcinol couplers can be prepared by reacting the potassium salt of an appropriate dihydroxybensoic acid with an appropriate bromide in the presence of a suitable catalyst such as a crown ether catalyst.

The color developing agent incorporated in the elements of the present invention can be any of the color developing agents typically employed for the development of color photographic materials. These developing agents are primary aromatic amines such as p-phenylenediamines and p-aminophenols. Exemplary of such color developing agents are p-aminophenol, 2,6-dichloro-4-aminophenol, 2,6-dibromo-4-aminophenol, 4-amino-N,N-dimethylaniline hydrochloride, 4-amino-N,N-diethylaniline hydrochloride, 4-amino-3-methyl-N,N-diethylaniline hydrochloride (N,N-diethyl-3- methyl-p-phenylene-diamine hydrochloride), 4-amino-N-ethyl-N-β-hydroxyethylaniline sulfate, 4-amino-3-methyl-N-ethyl-N-β-hydroxyethylaniline hydrochloride, 4-amino-3-methoxy-N-ethyl-Nβ-hydroxyethyaniline hydrochloride, 4-amino-N-butyl-N-γ-sulfobutylaniline, 4-amino-3-methyl-N-ethyl-N-β-sulfoethylaniline, 4-amino-3-β-(methanesulfonamido)ethyl-N,N-diethylaniline dihydrochloride, 4-amino-3-methyl-N-ethyl-N-β-(methanesulfonamido)ethylaniline sulfate, 4-amino-3-methyl-N-β-methoxyethylaniline di-p-toluene sulfonic acid, etc.

Alternatively, a precursor of a color developing agent can be employed. Such precursors are of the type in which the reactive site of the color developing agent is blocked in such a way that at elevated pH, such as found in the alkaline activator, the blocking group will cleave to yield the color developing agent. Schiff bases of color developing agents are exemplary of such color developing agent precursors. Suitable Schiff bases are described in Jan Jaeken U.S. Pat. No. 2,695,234 and Reeves U.S. Pat. No. 3,342,599, in which the free amine of a color developing agent is blocked with an alkali hydrolyzable divalent moiety.

Other Schiff bases which can be incorporated in the elements of this invention include Schiff bases of 2,6-dichloro-4-aminophenols and p-phenylene diamines obtained by reacting the color developing agent with an aryl aldehyde or heterocyclic aldehyde in water, methanol or benzene. The following are representative of such Schiff bases:

where R is:

 SB-1

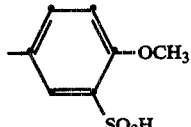 SB-2

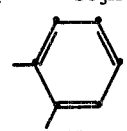 SB-3

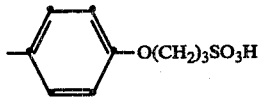

where R is:

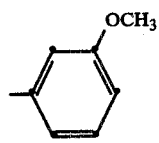 SB-4

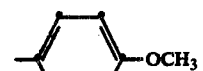 SB-5

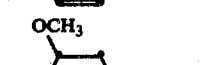 SB-6

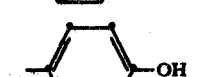 SB-7

 SB-8

 SB-9

 SB-10

 SB-11

 SB-12

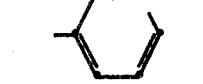 SB-13

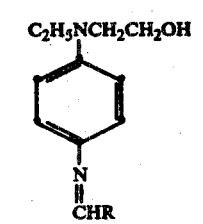

where R is:

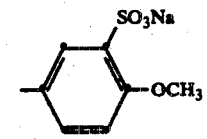 SB-14

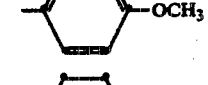 SB-15

 SB-16

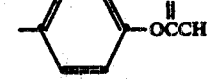 SB-17

-continued
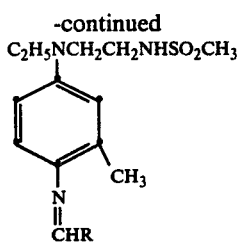
where R is:
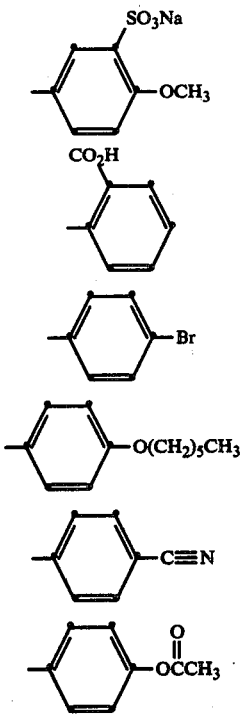
where R is:
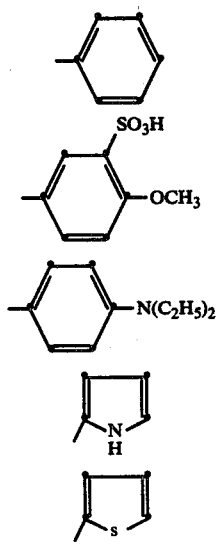
| | |
|---|---|
| SB-18 | |
| SB-19 | |
| SB-20 | |
| SB-21 | |
| SB-22 | |
| SB-23 | |
| SB-24 | |
| SB-25 | |
| SB-26 | |
| SB-27 | |
| SB-28 | |
-continued
 SB-29
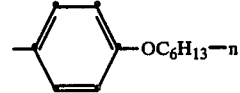 SB-30
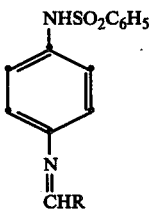
where R is:
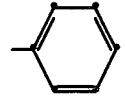 SB-31
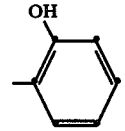 SB-32
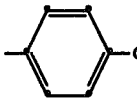 SB-33
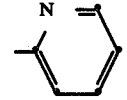 SB-34
where R is:
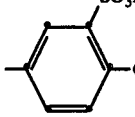 SB-35
SB-36
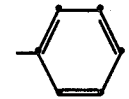 SB-37
SB-38

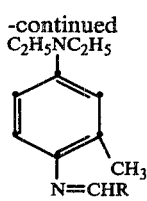

where R is:

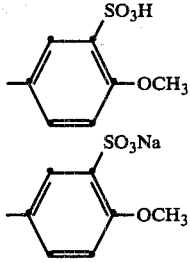

It has been found that the storage stability of the elements of this invention is improved if the primary aromatic amine color developing agent is present in its protonated form. Thus, it is particularly desirable to adjust the pH of the composition to a level at which the color developing agent is protonated. While the particular pH will depend upon the specific color developing agent incorporated in the composition, with most of the color developing agents contemplated for use in the present invention a pH in the range of 3 to 5 is sufficient to protonate the color developing agent. Such pH adjustment can be effected with any suitable mineral or carboxylic acid, for example citric, phosphoric, hydrochloric, sulfuric, and the like acids. Additionally, buffering agents can be incorporated in the composition to maintain the pH at this level.

The photographic silver halide emulsions employed in the elements of the present invention can be any of the silver halide emulsions employed in the art. They can comprise, for example, crystals of silver chloride, silver bromide, silver bromoiodide, silver chlorobromide, silver chloroiodide or silver chlorobromoiodide, or mixtures of such crystals. The emulsions can be coarse grain or fine grain and may be polydisperse or monodisperse. The emulsions can be negative emulsions or direct positive emulsions. They can be surface image emulsions which form a latent image predominantly on the surface of the silver halide grain or they can be internal image emulsions which form a latent image predominantly in the interior of the silver halide grain. If desired, mixtures of surface image emulsions and internal image emulsions can be employed.

The emulsions can be sensitized with chemical sensitizers, such as: reducing agents; sulfur, selenium or tellurium compounds; noble metals such as gold, palladium, platinum or rhodium compounds; or with combinations of such chemical sensitizers.

The silver halide emulsions can be spectrally sensitized with sensitizing dyes such as cyanine and merocyanine dyes to extend or enhance the sensitivity of the emulsion to given regions of the electromagnetic spectrum.

The silver halide coverage in the elements of this invention can vary over wide limits. Inasmuch as metallic silver does not provide the total image density, the silver halide coverage can be lower than that which would otherwise be required to provide an image of acceptable density. The silver halide coverage, however, can be that which is conventionally used for the preparation of black-and-white images for various purposes. Thus, the elements of the present invention can have silver halide coverages as low as 0.1 milligram of silver per square decimeter or lower and as high as 200 milligrams per square decimeter or higher. Preferred coverages would be in the range 2.0 to 20 milligrams per square decimeter.

Coverages at the lower end of the range would be particularly suitable if the elements are to be processed primarily by a redox amplification reaction in which the developed or latent image silver acts as a catalyst for the oxidation of the color developing agent by an oxidizing agent such as a transition metal complex (e.g. cobalt (III) hezammine) or a peroxide (e.g. hydrogen peroxide). Such processing is described in U.S. Pat. Nos. 3,674,490; 3,822,129; 3,834,907; 3,841,873; 3,847,619; 3,862,842; 3,902,905; and 3,923,511.

Inasmuch as the non-diffusible resorcinol couplers are four equivalent couplers, i.e., they require the reduction of four moles of silver for each mole of dye formed, the stoichiometric amount of coupler incorporated in the element would be about 0.25 mole of coupler for each mole of silver halide. Less than the stoichiometric equivalent of coupler could be employed, particularly if it were found that dye densities obtained with the element were too high for the use intended for the element. Alternatively, greater than the stoichiometric amount of coupler could be employed. This would be advantageous where the silver halide coverage is low or the developed silver is to be removed and it is desired that the greatest amount of dye formation possible be obtained. Thus, typically the elements would contain about 0.25 to about 0.75 mole of non-diffusible resorcinol coupler per mole of silver halide.

These stoichiometric relationships could obviously be varied when processing is primarily by a redox amplification reaction of the type referred to above. Coupler concentration set forth in U.S. Pat. No. 3,834,907 are exemplary of concentrations useful in redox amplification reaction.

The color developing agent or precursor thereof would generally be incorporated in the element in an amount equimolar with the coupler although more or less than the stoichiometric equivalent could be employed. Thus, preferred elements would contain 0.25 to 0.75 moles of color developing agent or color developing agent precursor per mole of silver halide.

As indicated above, the elements of this invention can advantageously incorporate additional addenda to further improve their properties. One such addendum is an electron transfer agent, which also is referred to in the art as a cross-oxidizing agent or a cross-oxidizing developer. It has been found that elements of this invention containing such electron transfer agents exhibit increased speed, and increased dye yield compared with equivalent elements not containing the electron transfer agent. Such an electron transfer agent can alternatively or additionally be in the alkaline activator solution. Electron transfer agents which are suitable for use in the present invention are those which have conventionally been employed as cross-oxidizing agents in color photographic elements. Typically, these compounds are black-and-white developing agents, which will develop exposed silver halide, but whose oxidation product will not couple with color couplers under the conditions at which development occurs. Preferred electron transfer agents for use in this invention are 3-pyrazolidone compounds such as 1-phenyl-3-pyrazolidone, 1-phenyl-4,4-dimethyl-3-pyrazolidone, 1-phenyl-2', 4,4-trimethyl-3-pyrazolidone, 4-hydroxymethyl-4-methyl-1-phenyl-3-pyrazolidone, 1-m-tolyl-3-pyrazolidone, 1-p-tolyl-3-pyrazolidone, 1-phenyl-4-methyl-3-pyrazolidone, 1-phenyl-5-methyl-3-pyrazolidone, 1-phenyl-4,4-bis-(hydroxymethyl)-3-pyrazolidone, 1,4-dimethyl-3-pyrazolidone, 4-methyl-3-pyrazolidone, 4,4-dimethyl-3-pyrazolidone, 1-(3-chlorophenyl)-4-methyl-3-pyrazolidone, 1-(4-chlorophenyl)-4-methyl-3-pyrazolidone, 1-(3-chlorophenyl)-3-pyrazolidone, 1-(4-chlorophenyl)-3-pyrazolidone, 1-(4-tolyl)-4-methyl-3-pyrazolidone, 1-(4-tolyl)-3-pyrazolidone, 1-(2-tolyl)-4-methyl-3-pyrazolidone, 1-(3-tolyl)-3-pyrazolidone, 1-(3-tolyl)-4,4-dimethyl-3-pyrazolidone, 1-(2-trifluoroethyl)4,4-dimethyl-3-pyrazolidone, 5-methyl-3-pyrazolidone and the like. If an electron transfer agent is employed, it can be present in an amount up to about 0.5 mole of electron transfer agent per mole of silver.

A further addendum, which may be useful to stabilize the color developing agent or its precursor, and hence improve storage stability of the element, is a water-soluble salt of a polyvalent metal such as nickel, zinc, cobalt, lead, barium, cerium, cesium, cadmium, and tin, particularly the nitrates, sulfates, sulfamates, sulfaminates, and citrates. Metal salts have previously been used to stabilize color developing agents as described in Barr et al U.S. Pat. No. 3,719,492. The metal salts employed in the present invention serve to stabilize not only the color developing agent but also precursors of color developing agents such as Schiff bases.

When incorporated in elements of the present invention, the metal salts are typically employed in the range of 0.001 to 0.02 moles of metal salt per mole of color developing agent or precursor.

We have found that some elements to which a polymeric latex is added yield increased dye density compared with similar elements not containing the latex. Other advantageous effects obtained when latexes are used with incorporated developing agents are described in *Research Disclosure*, August 1976, No. 14850, pp. 77–79. *Research Disclosure* is published by Industrial Opportunities Ltd., Homewell Havant, Hampshire, PO9 1EF, United Kingdom. Accordingly, in some instances it will be desirable to incorporate a latex into the compositions employed to make the elements of this invention. The latex is typically added to either or both of the non-diffusible resorcinol coupler and the color developing agent or color developing agent precursor prior to their being mixed together and incorporated into the elements.

Suitable latexes include homo-, co- and terpolymers of such monomers as styrene, ethyl acrylate, n-butyl acrylate, n-butyl methacrylate, 2-acetoacetoxyethyl methacrylate, 2-(methacryloyloxy)ethyltrimethyl ammonium methosulfate, 3-(methacryloyloxy)propane-1-sulfonic acid, sodium salt, N-isopropylacrylamide, N-[2-(2-methyl-4-oxopentyl)]acrylamide, 2-acrylamido-2-methylpropane sulfonic acid, and the like.

The amount of latex incorporated into the total composition will vary depending upon the particular latex employed. The controlling criterion should be that the latex should not be employed in an amount which will render the ultimate coating unduly soft for its intended use. Amounts of latex, on a weight basis, of up to about one-third of the amount of vehicle employed are generally suitable.

The vehicles useful in the elements of the present invention are the hydrophilic colloids commonly employed in photographic materials. Suitable hydrophilic colloids include both naturally occurring substances such as proteins, for example, gelatin, gelatin derivatives, cellulose derivatives, polysaccharide, such as dextran, gum arabic and the like; and synthetic polymeric substances such as water-soluble polyvinyl compounds like poly(vinylpyrrolidone), acrylamide polymers and the like.

The layer(s) of the element can be hardened with various organic or inorganic hardeners, alone or in combination, such as the aldehydes and blocked aldehydes described in Allen et al U.S. Pat. No. 3,232,764, ketones, carboxylic and carbonic acid derivatives, sulfonate esters, sulfonyl halides and vinylsulfonyl ethers as described in Burness et al U.S. Pat. No. 3,539,644, active halogen compounds, epoxy compounds, aziridines, active olefins, isocyanates, carbodiimides, and polymeric hardeners such as oxidized polysaccharides like dialdehyde starch and oxyguar gum.

The element can contain additional conventional addenda such as coating aids and surfactants, antioxidants, plasticizers and lubricants, matting agents, brighteners, etc.

The element can contain supports of a wide variety. Typical supports include cellulose ester film, polyvinyl acetal film, polystyrene film, polyethyleneterephthalate film, polycarbonate film and related films of resinous materials as well as glass, paper, metal and the like. Typically, a flexible support is employed. When the support is a paper support, it is particularly desirable that the support be coated with baryta and/or an α-olefin polymer, particularly a polymer of an α-olefin containing 2 to 10 carbon atoms such as polyethylene, polypropylene, ethylene-butylene copolymers and the like.

The element can contain additional layers such as subbing layers, overcoat layers, antistatic layer and the like which conventionally are utilized in photographic elements.

The elements of this invention can be prepared by conventional techniques. Typically, a coating composition containing the various components is prepared, coated on a suitable support and dried, observing the precautions normally taken with light sensitive silver halide materials. Preferably, all of the components are coated as a single layer on one or both sides of the support. However, it is contemplated that the components of the coating composition can be divided between two or more layers on the same side of the support. For example, the silver halide emulsion and the non-diffusible resorcinol coupler can be contained in separate layers with the color developing agent or color developing agent precursor and the electron transfer agent (if one is employed) contained in either or both of the layers.

The photographic elements of this invention can, after imagewise exposure, be processed to yield visible images of neutral density by a simple processing sequence using uncomplicated compositions. The only necessary step is activation of the exposed element with an alkaline activator composition. Additional optional steps, in the sequence they can be employed, are: further development with a non-dye-forming silver halide developing agent; treatment with an acid stop bath; fixing and/or bleaching; and treatment with an alkaline composition (as described below). Certain of these additional steps can be combined by using processing solutions which serve more than one function. For example the further development step and the fix step can be combined by using a monobath which develops and fixes; or the fixing and bleaching steps can be combined by using a bleach-fix bath.

With a negative emulsion this processing sequence leads to a negative image, i.e. an image in which dye is formed in areas of light exposure in an amount directly proportional to the amount of light exposure. With a direct positive emulsion this processing sequence leads to a positive image.

Positive images can be obtained with negative emulsions by preceding the alkaline activation step with two additional steps; namely, (1) development with a solution containing a separate developing agent to form a negative silver image in the element, but no dye image, followed by (2) uniform fogging of the residual silver halide, either with light or a nucleating agent, to form a developable latent image in the initially unexposed areas. When the element is then contacted with the alkaline activator composition, coupling occurs only in the fogged areas, resulting in a positive dye image. Typically, this first development step will be performed with a developing agent and at a pH which will not result in coupling of the ballasted resorcinol coupler and the oxidized developing agent formed during this step.

Inasmuch as the processing sequence leading to a positive image with a negative emulsion results in a uniform silver density throughout the element, bleaching of the silver is desirable unless the silver coverage is sufficiently low so as to provide an unobjectionally low uniform density in background areas.

The black-and-white photographic elements of this invention can be activated with any suitable alkaline activator composition which will provide an environment sufficiently alkaline to cause conversion of the color developing agent precursor (if one is employed) to a color developing agent, to promote the reduction of developable silver halide to metallic silver by the color developing agent and/or the electron transfer agent, if present, and to favor the coupling of the oxidized color developing agent with the non-diffusible resorcinol coupler.

Any source of hydroxyl ions which will raise the pH of the element to an appropriate level, e.g. pH 11 to pH 14, is suitable. The optimum pH will depend upon the particular combination of non-diffusible resorcinol coupler and color developing agent or color developing agent precursor. Thus, the alkaline activator could be as simple a composition as an aqueous solution of an appropriate base, such as an inorganic base like sodium hydroxide, sodium carbonate, potassium hydroxide, etc.

Preferably the alkaline activator will contain in addition such components as a solvent for the color developing agent, e.g. benzyl alcohol, ethyl acetate, dimethyl formamide, etc.; a development accelerator such as an amine, e.g. 2-(2-aminoethylamino)ethanol, 11-aminoundecanoic acid, hydroxylamine, 2-diethylaminoethanol, 2-dimethylaminoethanol, triethanolamine, etc., optionally in combination with a quaternary ammonium salt such as tetramethyl ammonium bromide; and an antifoggant such as potassium bromide, 5-methylbenzotriazole, 4-carboxythiazoline-2-thione.

Additionally, the alkaline activator can contain a fixing agent so as to avoid the need for an additional fix step, or can contain a non-dye-forming silver halide developing agent, or can contain both a fixing agent and a non-dye-forming silver halide developing agent.

Alkaline activation can be performed at a temperature and for a time sufficient to develop in the exposed element a visible image of acceptable density. Such results can be achieved by processing at times of several seconds to several minutes, e.g. 3 seconds to 5 minutes, and at room temperature (20° C.) or at elevated temperatures, e.g. up to about 50° C.

We have found that with certain of the couplers employed in the present invention the inclusion in the alkaline activator composition of a complex of a polyvalent metal increases dye yield. Therefore, in some instances it is desirable to incorporate such a complex in the alkaline activator composition, particularly if the silver image is faint or ultimately is to be bleached out of the element.

Preferred complexes of polyvalent metals are cobalt (III) complexes having a coordination number of 6 and have mono- or bidentate ligands chosen from among ligands such as alkylenediamine, ammine, aquo, nitrate, nitrite, azide, chloride, thiocyanate, isothiocyanate, carbonate and similar ligands commonly found in cobalt (III) complexes. Especially useful are the cobalt (III) complexes comprising four or more ammine ligands, such as $[Co(NH_3)_6]X$, $[Co(NH_3)_5-H_2O]X$, $[Co(NH_3)_5(CO_3)]X$, $[Co(NH_3)_5Cl]X$ and $[Co(NH_3)_4CO_3]X$, wherein X represents one or more anions determined by the charge neutralization rule and X preferably represents a polyatomic organic anion. Such complexes are further described in Mowrey U.S. Pat. No. 3,904,413.

In place of a complex of a polyvalent metal, peroxide or peracid compounds, such as described in Matejec U.S. Pat. No. 3,674,490, can be employed. A preferred peroxide compound is hydrogen peroxide.

It has been found that if alkaline activation does not fully develop the silver halide in image areas, further development with a solution containing a non-dye-forming silver halide developing agent will provide additional silver density. Where such additional silver density is desired, further development can be carried out as a separate step using a solution containing a non-dye-forming silver halide developing agent or as a combined step using a monobath which will perform the further development step and another step, such as fixing.

After alkaline activation and any further development the element can be placed in an acid bath to lower the pH and terminate development. When color development agent precursors are employed which are colored, such as certain Schiff bases, an acid bath is desirable so as to hydrolyze the colored component to colorless products which can be washed out of the element.

If desired, the element can be fixed, fixed and bleached, or bleach-fixed to remove residual silver halide or both developed silver and residual silver halide. Compositions and solutions which are conventionally employed in photography can be used for such purposes.

We have found that a shift in hue and density of the image dye may occur with certain of the compositions of the present invention from which silver has been removed oxidatively, for example by bleaching or bleach-fixing. In such instances, the original hue and density can be regenerated by briefly treating the element with an alkaline solution such as the alkaline activator composition which was employed to develop an image in the element.

The following preparations and examples are included for a further understanding of this invention.

PREPARATION 1 —
2',6'-Dihydroxy-4-n-octylbenzanilide — Compound RC-24

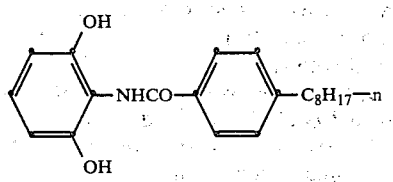

A solution of 10 g (0.06 mole) of 2-nitroresorcinol in 160 ml of degassed tetrahydrofuran was reduced over 10% Pd/C catalyst in a Parr apparatus at ambient temperature and 57 p.s.i. of hydrogen. Under a nitrogen atmosphere the reaction mixture was filtered into a solution of 16.4 g (0.06 mole) of p-octylbenzoyl chloride and 7.9 g (0.06 mole) of N,N-dimethylaniline in 100 ml of degassed tetrahydrofuran. After standing for one day at room temperature under nitrogen the solvent was removed in vacuo. The resulting yellow-brown oil was dissolved in ethyl acetate, washed once with 10% hydrochloric acid, once with water, and dried over magnesium sulfate. The solution was treated with charcoal and evaporated. The solid residue was slurred in ligroin and filtered to yield 12 g (54.5%) of an off-white solid. Two recrystallizations from acetonitrile afforded 11 g of pure product, m.p. 125°–126° C.

PREPARATION 2 —
2',6'-Dihydroxy-3',5'-dibromo-4-n-decylbenzanilide — Compound RC-29

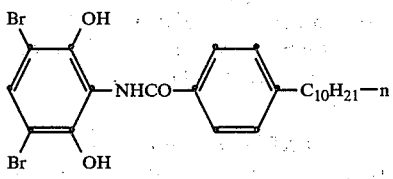

To a solution of 11 g (0.03 mole) of 2',6'-dihydroxy-4-n-decylbenzanilide (prepared as in Preparation 1) in 200 ml of chloroform was added dropwise over a period of about 20 minutes, a solution of 9.6 g (0.06 mole) of bromine in 50 ml of chloroform. Stirring was continued for one-half hour after which thin layer chromatography (TLC) indicated no starting benzanilide was present. Concentration to dryness gave a solid which was recrystallized from acetonitrile providing a pinkish solid, m.p. 117°–119° C. (melts orange). Recrystallization from acetonitrile gave 8.3 g of very light pinkish crystalline product m.p. 117°–119° C.

PREPARATION 3 —
2',6'-Dihydroxy-2-methoxybenzanilide — Compound RC-31

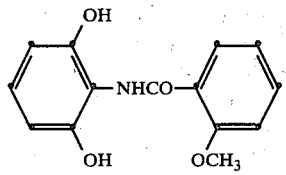

2-Aminoresorcinol hydrochloride (25 g) was combined with triethylamine (25 g) in acetonitrile (400 ml). With stirring, o-methoxybenzoyl chloride (25.6 g) was added. The mixture was stirred at room temperature overnight, then concentrated to dryness to yield a very dark residue which was treated with dilute hydrochloric acid. After stirring briefly, the aqueous layer was decanted. The residue was then dissolved in ethyl acetate in a separatory funnel and the extracts washed three times with water. The extracts were then dried using magnesium sulfate, filtered, then concentrated to dryness. The dark brown-to-black residue which remained was recrystallized from acetonitrile using decolorizing carbon (Nuchar). This provided 12.4 g of crystalline product (m.p. 223°–225° C.).

PREPARATION 4 —
3',5'-Dihydroxy-4-n-pentoxybenzanilide — Compound RC-34

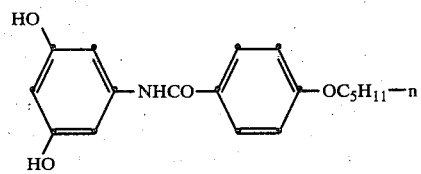

To 100 ml of acetic acid were added 12.5 g (0.1 mole) of 3,5-dihydroxyaniline followed by 9.8 g (0.1 mole) of potassium acetate. To this was added in one portion and with stirring 22.6 g (0.1 mole) of p-n-pentyloxybenzoyl chloride. After stirring at room temperature overnight the precipitate was collected and washed with acetic acid, with hexane, collected, dried, and then dissolved in ethyl acetate and washed with water, with aqueous hydrochloric acid and then thrice with water. The extracts were dried using magnesium sulfate, filtered, and the filtrate concentrated to dryness. The white solid residue which remained was recrystallized from acetonitrile providing 11.1 g of white solid product m.p. 185°–187° C.

PREPARATION 5 —
2',4'-Dihydroxy-4-n-pentoxybenzanilide — Compound RC-36

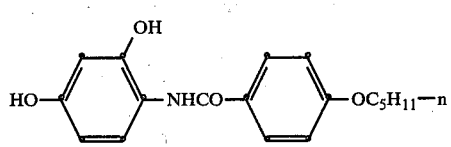

To a mixture of 16.2 g (0.1 mole) of 4-amino-resorcinol hydrochloride in 240 ml tetrahydrofuran were added 25 g (0.2 mole) of N,N-dimethylaniline. A solution of 22.6 g (0.1 mole) of p-n-pentyloxybenzoyl chloride in 100 ml of tetrahydrofuran was added dropwise with stirring. After stirring at room temperature overnight, the insolubles were filtered off and discarded. Concentration of the filtrate to dryness provided a golden residue. The residue was dissolved in ethyl acetate, washed with dilute hydrochloric acid, then thrice with water. The extract was dried with magnesium sulfate, filtered, and the filtrate concentrated to dryness. Hexane was added to the residue which remained, and after stirring for several minutes, a solid was collected, dried, then recrystallized from acetonitrile providing 2.8 g of fine white solid, m.p. 180°–182° C.

PREPARATION 6 —
N-(2,6-Dihydroxyphenyl)cinnamamide — Compound RC-52

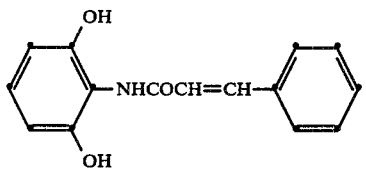

To a solution of 0.1 mole of 2-aminoresorcinol in 150 ml of dry tetrahydrofuran were added 12.1 g (0.1 mole) of N,N-dimethylaniline followed by a solution of 16.6 g (0.1 mole) of cinnamoyl chloride in 50 ml of tetrahydrofuran. After stirring at room temperature over night the clear dark solution was concentrated to dryness. Addition of water and concentrated hydrochloric acid resulted in rapid solidification. After standing overnight the yellowish solid was collected and dried. Recrystallization from acetonitrile using Nuchar decolorizing carbon provided 13.4 g of yellow crystalline solid, m.p. 210°–212° C. Another recrystallization provided 10.2 g of white glittering crystalline product m.p. 212°–214° C. (melts clear with golden color).

PREPARATION 7 —
2',6'-Dihydroxy-4-octylbenzanilide Compound RC-61

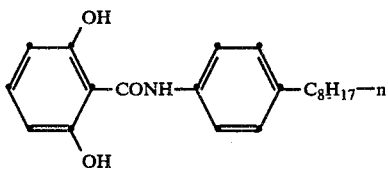

p-Octylaniline — Concentrated sulfuric acid (80 ml) was cooled in an ice/methanol bath and 200 g (1.06 mole) of 1-phenyloctane was added. A mixture of concentrated nitric acid (70.8 ml) in concentrated sulfuric acid (121.6 ml) was added dropwise over a period of 5 hours at a rate to maintain the temperature between −10° and 5° C. After stirring in the ice/methanol bath overnight, the resulting brown slush was poured onto ice and extracted with ethyl acetate. The extract was washed with water, with dilute sodium hydrogen carbonate, and dried over sodium sulfate. Concentration to dryness afforded 240 g of an orange oil which was distilled at 90°–103° C./50 microns to yield 215 g of the slightly crude p-octylnitrobenzene.

A solution of 209 g (0.89 mole) of the above nitro compound in 500 ml of ethanol was reduced over 10% Pd/C at room temperatuure and 56 p.s.i. of hydrogen. After filtration of the catalyst, the solvent was removed in vacuo and the residual red oil was dissolved in ligroin. Concentrated hydrochloric acid was added. After refrigerating overnight, 107 g of the hydrochloride salt was collected as a pale pink solid. Recrystallization from benzene/ligroin yielded 75 g of fluffy white needles m.p. 78°–80° C.

2',6'-Dihydroxy-4-n-octylbenzanilide — To a solution of p-octylaniline hydrochloride (25 g, 0.12 mole) and quinoline (31.0 g, 0.24 mole) in 400 ml of tetrahydrofuran was added 30.8 g of 2,6-diacetoxybenzoyl chloride (0.12 mole). The resulting mixture was stirred at room temperature under nitrogen overnight. The insoluble salts were removed by filtration and the filtrate was evaporated to dryness. The residue was dissolved in ethyl acetate, washed once with 10% hydrochloric acid, once with water and dried over magnesium sulfate. After evaporation to dryness, the solid yellow residue was added to a solution of 25 g of sodium carbonate in 200 ml of water and 200 ml of ethanol and refluxed with stirring overnight. The reaction mixture was concentrated to ½ volume, acidified with concentrated hydrochloric acid and extracted with ethyl acetate. The extract was washed with water, dried over magnesium sulfate, treated with charcoal and evaporated to dryness. The resulting solid was slurried in ligroin and filtered. The recrystallization solvent was chloroform and the product was obtained in 15% yield as a white powder, m.p. 131°–133° C.

PREPARATION 8 —
N-(2,6-Dihydroxyphenyl)-N'-(2,5-dimethylphenyl)urea — Compound RC-63

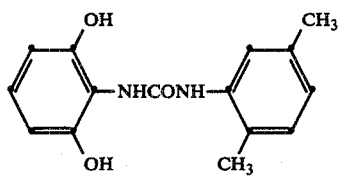

To a solution of 0.1 mole of 2-aminoresorcinol in 300 ml of tetrahydrofuran were added dropwise 14.7 g (0.1 mole) of 2,5-dimethylphenyl isocyanate. After stirring at room temperature overnight a small amount of precipitate was filtered and discarded. The filtrate was concentrated to dryness providing a white solid, m.p. 180° C. dec. After recrystallization from acetonitrile, 7.5 g of white solid product were obtained, m.p. 186°–188° C. dec.

PREPARATION 9 —
2-n-Hexadecylsulfonamidoresorcinol — Compound RC-65

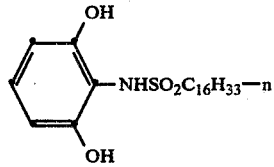

To a solution of 250 ml of dimethylformamide and 32 g of pyridine was added 32.3 g (0.2 mole) of 2-aminoresorcinol hydrochloride. A solution of 65 g of hexadecanesulfonyl chloride in 300 ml of dimethyl formamide was added dropwise with stirring. The reaction mixture was stirred at room temperature overnight after which it was slowly poured into ice/water containing hydrochloric acid. The precipitate which formed was collected, dried, then dissolved in ethyl acetate and washed with water. The ethyl acetate extracts were dried using magnesium sulfate, filtered, and the filtrate concentrated to dryness. The brownish solid which remained was recrystallized from acetonitrile and provided 12.3 g of fine tan powder m.p. 105°–110° C. Another recrystallization from acetonitrile using Nuchar decolorizing carbon gave 5.2 g of white solid m.p. 116°–118° C.

PREPARATION 10 —
p-t-Pentylphenyl-2,6-dihydroxybenzoate — Compound RC-67

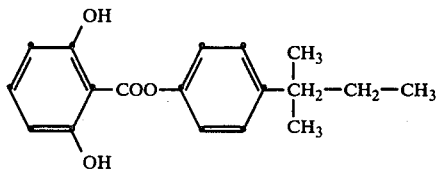

A slurry of 2,6-dihydroxybenzoic acid (30 g, 0.2 mole) and p-t-pentylphenol (41 g, 0.4 mole) in phosphorus oxychloride (61.2 g, 0.4 mole) was stirred and heated on a steam bath for 4 hours. The resulting mixture was poured onto ice. When the ice was melted, the aqueous mixture was extracted with ethyl acetate, and the extract was washed with water and dried over magnesium sulfate. After evaporation to dryness, the resulting dark brown oil was dissolved in chloroform and filtered. Evaporation of the chloroform from the filtered solution afforded a pale yellow oil which was triturated with ligroin, cooled and filtered to yield 11g of white crystals. The product was recrystallized twice from ligroin/chloroform, m.p. 95°–97° C.

PREPARATION 11 —
n-Decyl-2,6-dihydroxybenzoate — Compound RC-70

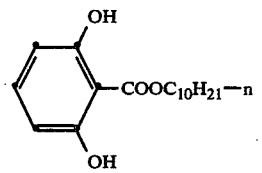

Tetra-iso-propyl orthotitanate (2 drops) was added to a mixture of 16.8 g (0.1 mole) of methyl-2,6-dihydroxybenzoate in 100 ml of dry (distilled) decyl alcohol. The solution was refluxed via a partial condensing still for 1.5 hours (until the theoretical amount of methanol had distilled off). The system was protected from moisture with a calcium sulfate drying tube. Excess decyl alcohol was removed by distillation under aspirator pressure (123°–126° C.). The remaining partially solidified residue was taken up in benzene and filtered through about 50 g of florisil. Evaporation to dryness afforded a yellow oil which was dissolved in 30 ml of ligroin and cooled in a freezer. The filtered precipitate was recrystallized from ligroin to give a 68% yield in the form of white flakes m.p. 36°–38° C.

EXAMPLE 1

A coating composition was prepared as follows: 70.0 ml of 12% deionized pigskin gelatin was mixed with 1.6 g of nickel(ous) nitrate hexahydrate and stirred until the nickel salt was dissolved. Next, 0.5 g of the electron transfer agent 2′,4,4-trimethyl-1-phenyl-3-pyrazolidone was dissolved in 10.0 ml methanol and stirred into the gelatin solution. The Schiff base SB-39, p-(benzylideneamino-4-methoxy-3-sulfonic acid)-N,N-diethyl-3-methyl aniline, (2.0 g) and the latex copolymer of n-butyl acrylate (85), 3-methacryloyloxy-propane-1-sulfonic acid sodium salt (10) and 2-acetoacetoxyethyl methacrylate(5) (20.0 ml of a 17.5% solution adjusted to pH 7) were mixed and added to the gelatin solution. 10 ml of a 2% solution of bis(vinylsulfonylmethyl)ether hardener was added to the solution.

A coupler dispersion was prepared by mixing 1.6 g of resorcinol coupler RC-31, 2′,6′-dihydroxy-2-methoxybenzanilide, in 6.0 ml of N,N-diethyldodecanamide coupler solvent and 6.0 ml of ethyl acetate. The coupler-solvent mixture was stirred into a mixture of 30.0 ml of 12% deionized pigskin gelatin, 30.0 ml of distilled water and 10.0 ml of the above described latex copolymer. The resulting mixture was dispersed in a colloid mill and then was added to the gelatin composition containing the Schiff base.

Then, 4.0 ml of a 10% solution of a nonylphenoxyglycidol surfactant (Surfactant 10G, trademark) and 16.4 ml of a silver chlorobromide emulsion (0.9 kg/mole) were added to the gelatin solution.

This composition was coated on a gel-subbed paper support to provide a coverage of 134.5 ml/m$^2$. The coated element was chill-set and forced-air dried with a maximum dryer temperature of 50° C.

Silver coverage was 16 mg/dm$^2$.

A portion of the element was exposed through a 0 to 3 density step wedge (0.3 density increments) with a 1.0 neutral density filter between the light source and the step wedge using an EG & G Sensitometer, Mark VI, at a setting of 10$^{-3}$ seconds. The energy reaching the Step 1 area of the element was about 631 ergs.

The element was processed at 24° C. as follows:
1. Activation of the exposed element for 15 seconds in an aqueous solution of 1% sodium hydroxide, 0.1% potassium bromide and 0.5% cobalt hexammine chloride.
2. Decolorization of the residual Schiff base in the element for two minutes in 1% cyclohexylsulfamic acid.
3. Bleaching and fixing the silver in the element for two minutes in Bleach-Fix Solution A, shown below.
4. Washing one minute at 21° C.
5. Reactivation for ten seconds in the solution of Step 1.
6. Washing five minutes at 21° C.

The visual effect was a good neutral image with $D_{max}$ of 2.0 and $D_{min}$ of 0.15. Residual silver was less than 0.3 mg/dm$^2$ in the $D_{max}$ area. A spectrophotometric absorption trace of the dye image between 420 and 650 nanometers varied less than 5%

| Bleach Fix Solution A | |
| --- | --- |
| Ammonium Thiosulfate | 132 g |
| Sodium Bisulfite | 13 g |
| Ammonium ferric ethylene-diamine tetraacetic acid (0.18M solution) | 65.6 g |
| Ethylene diamine tetraacetic acid | 6.56 g |
| 28% Ammonium hydroxide | 27.9 g |
| Water (pH 6.8 at 22° C) | To 1 liter |

EXAMPLE 2

Using resorcinol coupler RC-70 the following composition was prepared:

| | |
| --- | --- |
| Gelatin | 6.0 g |
| Water | 96.0 ml |
| Surfactants: the sodium salt of an alkylaryl polyether sulfate (Triton 770, Trademark) | 0.18 g |

| | |
|---|---|
| the sodium salt of an alkylarylpolyether sulfonate Triton X-200, trademark) | 0.30 g |
| Coupler RC-70 | 1.75 g |
| N,N-diethyl-3-methyl-paraphenylenediamine hydrochloride | 1.45 g |
| Bis(vinylsulfonyl methyl)ether | 0.30 g |
| pH adjusted to 4.0 with citric acid | |
| Silver bromide emulsion sensitized to green radiation (as silver) | 1.80 g |

This composition was coated on clear polyethylene terephthalate film support and dried. Silver coverage was 12 mg/dm$^2$.

A portion of the resulting element was given simulated X-ray exposure according to the standard procedure described in Bulletin ANSI-PH 2.9, 1974, published by the American National Standards Institute. The test object was a standard 0 to 3.0 density step wedge having 0.3 density increments. The exposing unit was a Kodak Model 101 Processing Control Sensitometer. Exposure time was 1/5 second to a tungsten light source through a filter combination of a Corning 4010 filter and a 1.0 neutral density filter. The exposed element was then activated for 30 seconds at 22° C. in an aqueous activator solution of 10 g/l sodium hydroxide and 1 g/l potassium bromide. The element was fixed in a solution containing 120 ml/l of a 60% solution of ammonium thiosulfate, 2.6 g/l sodium bisulfite and 4.0 g/l sodium sulfite. A neutral density image resulted. Transmission density in the area of maximum exposure was 1.44; 0.82 part was from silver and 0.62 part was from dye.

EXAMPLE 3

Using resorcinol coupler RC-24 the following composition was prepared:

| | |
|---|---|
| Water | 103.00 ml |
| Gelatin | 6.00 g |
| Latex copolymer of 90 mol % n-butyl acrylate and 10 mol % 2-acrylamido-2-methylpropane sulfonic acid | 2.00 g |
| Coupler RC-24 | 2.00 g |
| 2′,4,4-Trimethyl-1-phenyl-3-pyrazolidone (electron transfer agent) | 0.50 g |
| N,N-Diethyldodecanamide | 4.00 g |
| Ascorbic acid | 0.04 g |
| N,N-Diethyl-3-methylparaphenylenediamine hydrochloride | 1.45 g |
| Nickel sulfate hexahydrate | 1.40 g |
| Bis(vinylsulfonylmethyl)ether (hardner) | 0.30 g |
| Silver bromide emulsion, sensitized to green radiation (as silver) | 1.80 g |

The composition was coated onto a transparent, blue tinted, gel-subbed polyethylene terephthalate film support and dried. Silver coverage was 11 mg/dm$^2$. A portion of the resulting element was given a simulated X-ray exposure according to the standard procedure described in Bulletin ANSI-PH 2.9, 1974, published by the American National Standards Institute. The test object was a standard 0 to 3.0 density step wedge having 0.3 density increments. The exposing unit was a Kodak Model 101 Processing Control Sensitometer. Exposure time was 1/5 second to a tungsten light source through a filter combination of a Corning 4010 filter and a 1.0 neutral density filter. The exposed element was then activated for 30 seconds at 22° C. in an aqueous solution containing 1% potassium hydroxide, 1% benzyl alcohol, 0.1% potassium bromide, 2% sodium sulfite, and 0.5% 2-(2-aminoethylamino)ethanol. The element was fixed in the fix solution employed in Example 2 for 60 seconds at 22° C. Then one part of the $D_{max}$ area of the element was treated with methyl alcohol to remove dye image. Both parts were then washed and dried. A neutral image was obtained. The maximum transmission density was 2.02 for the silver plus dye image. The maximum transmission density in areas where dye was removed was 1.09 yielding a net dye density of 0.93.

EXAMPLE 4

Using Resorcinol Coupler RC-70 the following composition was prepared:

| | | | |
|---|---|---|---|
| Part A | 15% Deionized pigskin gelatin | 20 | ml |
| | Water | 12 | ml |
| | 10% Solution of a sodium alkyl naphthalene sulfonate surfactant (Alkanol X-C, trademark) | 0.1 | ml |
| | N,N-Diethyldodecanamide | 1.6 | ml |
| | 4-Methyl-4-hydroxymethyl-1-phenyl-3-pyrazolidone | 0.51 | g |
| | Coupler RC-70 | 1.85 | g |
| Part B: | 15% Deionized pigskin gelatin | 15 | ml |
| | Water | 5 | ml |
| | 2% Ascorbic acid | 2 | ml |
| | N,N-Diethyl-3-methylparaphenylenediamine hydrochloride | 1.35 | g |
| | Zinc chloride | 0.5 | g |
| | Ethanol | 5 | ml |
| Part C: | 2% Aqueous solution of Bis(vinylsulfonylmethyl)ether | 15 | ml |
| | 6.7% Aqueous solution of the sodium salt of an alkaryl polyether sulfonate (Triton X 200, trademark) | 3 | ml |
| | Silver bromoiodide emulsion (102 mgAg$^+$/ml) | 24.5 | ml |

Part A was prepared by dissolving the coupler and the 3-pyrazolidone in the diethyldodecanamide and adding to it the gelatin-water-surfactant mixture. Part A was then milled in a colloid mill.

Part B was prepared by mixing the components in the order listed and then was added to Part A. The pH was adjusted to 4.0 with 50% citric acid, and then Part C was added.

The resulting composition was coated on blue-tinted, gelatin-subbed polyethylene terephthalate film support. Silver coverage was 14 mg/dm$^2$.

A portion of the resulting element was given simulated X-ray exposure according to the standard procedure described in Bulletin ANSI-PH 2.9, 1974 published by the American National Standards Institute. The test object was a standard 0 to 3.0 density step wedge having 0.3 density increments. The exposing unit was a Kodak Model 101 Processing Control Sensitometer. Exposure time was 1/5 second to a tungsten light source through a filter combination of a Corning 5850 filter and a 1.0 neutral density filter. The exposed element was then activated for 30 seconds at 22° C. in an aqueous solution containing 1% sodium hydroxide, 1% benzyl alcohol, 0.1% potassium bromide, 2% sodium sulfite, 0.5% 2-(2-aminoethylamino)ethanol and 0.02% orthomercapto benzoic acid. The element was fixed as in Example 3. The element was then washed and dried. A neutral density image was obtained. Transmission density in the areas of maximum exposure was 1.80.

EXAMPLE 5

Using Resorcinol Coupler RC-70 the following composition was prepared:

| Part A | 15% Deionized pigskin gelatin | 20 | ml |
|---|---|---|---|
| | Water | 12 | ml |
| | 17% Solution of a latex copolymer of 90 mol % n-butyl acrylate and 10 mol % acrylamido-2-methylpropane Sulfonic acid | 3.5 | ml |
| | N,N-Diethyldodecanamide | 0.75 | ml |
| | 1-Phenyl-3-pyrazolidone | 0.5 | g |
| | Coupler RC-70 | 1.85 | g |
| Part B | 15% Deionized pigskin gelatin | 16 | ml |
| | Water | 11 | ml |
| | 2% Ascorbic acid | 2 | ml |
| | N,N-Diethyl-3-methylparaphenylenediamine hydrochloride | 1.35 | g |
| | Ethanol | 5 | ml |
| Part C: | 2% Aqueous solution of Bis(vinylsulfonylmethyl)ether | 15 | ml |
| | 6.7% Aqueous solution of the sodium salt of an alkaryl polyether sulfonate (Triton X 200, trademark) | 3 | ml |
| | Silver bromoidode emulsion (122 mgAg$^+$/ml | 20.5 | ml |

Part A was prepared by dissolving the coupler and the 3-pyrazolidone in the diethyldodecanamide and adding to it the gelatin-water-latex mixture. Part A was then milled in a colloid mill.

Part B was prepared by mixing the components in the order listed and then was added to Part A. The pH was adjusted to 4.0 with 50% citric acid, and then Part C was added.

The resulting composition was coated on blue-tinted, gelatin-subbed polyethylene terephthalate film support. Silver coverage was approximately 12 mg/dm$^2$.

A portion of the resulting element was given simulated X-ray exposure according to the standard procedure described in Bulletin ANSI-PH 2.9, 1974 published by the American National Standards Institute. The test object was a standard 0 to 3.0 density step wedge having 0.15 density increments. The exposing unit was a Macbeth Sensitometer. Exposure time was 1/50 second to a tungsten light source through a filter combination of a Wratten 39 filter and a 0.9 neutral density filter. The exposed element was then activated for 30 seconds at 22° C. in an aqueous solution containing 1% sodium hydroxide, 1% benzyl alcohol, 0.1% potassium bromide, 0.5% 2-(2-aminoethylamino)ethanol and 0.01% 5-methyl benzotriazole. The element was then treated with a monobath having the following composition after which it was washed and dried.

| Water | 750 ml |
|---|---|
| Sodium sulfite - anhydrous | 50 g |
| 1-Phenyl-3-pyrazolidone | 4 g |
| Hydroquinone | 12 g |
| Sodium hydroxide | 4 g |
| Sodium thisosulfate . 5 H$_2$O | 110 g |
| 25% Glutaraldehyde | 8 ml |
| Water | to 1 liter |

A neutral density image was obtained. Transmission density in the areas of maximum exposure was 2.05.

EXAMPLE 6

Using resorcinol coupler RC-31, the following composition was prepared:

| Part A | | |
|---|---|---|
| Deionized pigskin gelatin (12% solids) | 40.0 | ml |
| Nickel(ous) nitrate hexahydrate | 0.8 | g |
| Schiff base (See Table I) | 0.002 | mole |
| Latex copolymer of 80 mol % n-butylacrylate and 20 mol % 2-acrylamido-2-methyl propane sulfonic acid (17.8% solids with pH adjusted to 7.0) | 5.0 | ml |
| Direct positive AgBrI emulsion(45 mg Ag$^+$/ml) | 20.0 | ml |
| Part B | | |
| Resorcinol Coupler RC-31 | 0.8 | g |
| N,N-Diethyldodecanamide | 3.0 | ml |
| Ethylacetate | 3.0 | ml |
| Latex of Part A | 10.0 | ml |

Part B was milled in a colloid mill and then added to Part A. Then 2 ml of a nonylphenoxypolyglycidol surfactant (10% solids) and 3 ml of bis(vinylsulfonylmethyl) ether hardener (2% solids) were added to the composition, it was stirred, coated onto a gel-subbed polyethylene terephthalate film support and dried. Silver coverage of the dried coating was 7 mg/dm$^2$. Portions of the resultant elements were exposed twice through a 0 to 3.0 density step tablet with 0.3 density increments at a setting of $10^{-3}$ seconds on an EG & G Sensitometer, Mark VI. The exposed elements were processed in the following manner:

1. 20 seconds, 24° C. — 1% sodium hydroxide, 1% benzyl alcohol, 0.5% cobalthexammine chloride and 0.1% potassium bromide
2. 60 seconds, 24° C. — 2% cyclohexylsulfamic acid
3. 120 seconds, 24° C. — Bleach Fix Solution A described in Example 1
4. 60 seconds, 24° C. — water wash
5. 15 seconds, 24° C. — treat as in Step 1
6. Rinse and dry.

Each of the resultant dye images was neutral. Maximum and minimum transmission densities were:

TABLE I

| Schiff Base | D$_{min}$ | D$_{max}$ |
|---|---|---|
| SB-1 | 0.06 | 0.42 |
| SB-24 | 0.10 | 0.32 |
| SB-39 | 0.05 | 0.42 |

EXAMPLE 7

Following the procedure of Example 1, compositions were prepared and coated on gel-subbed paper supports to yield the following coverages:

| Component | mg/dm$^2$ |
|---|---|
| Deionized pigskin gelatin | 80.2 |
| Nickel(ous) nitrate | 10.7 |
| 2',4,4-Trimethyl-1-phenyl-3-pyrazolidone | 3.3 |
| Schiff Base SB-39 | 13.4 |
| Resorcinol Coupler (See Table II, below) | 10.7 |
| Latex copolymer of Example 1 | 35.1 |
| Silver bromoiodide emulsion (as silver) | 16.1 |

In the same way a second series of compositions was prepared having a lower proportion of silver halide and coated on gel-subbed paper supports to yield the following coverages:

| Component | mg/dm$^2$ |
|---|---|
| Deionized pigskin gelatin | 66.6 |
| Nickel(ous) nitrate | 8.9 |
| 2',4,4-Trimethyl-1-phenyl-3-pyrazolidone | 2.8 |
| Schiff Base SB-39 | 11.1 |
| Resorcinol Coupler (see Table III, below) | 8.9 |
| Latex copolymer of Example 1 | 26.6 |
| Silver bromoidide emulsion (as silver) | 4.9 |

The resultant elements were exposed and processed as in Example 1 to yield neutral density dye images as follows:

TABLE II

| Resorcinol Coupler | $D_{max}$ | Image Hue |
|---|---|---|
| RC-2 | 2.06 | Neutral |
| RC-18 | 1.72 | Neutral |
| RC-20 | 1.64 | Neutral |
| RC-28 | 1.82 | Neutral |
| RC-31 | 2.10 | Neutral |
| RC-35 | 2.14 | Neutral |
| RC-63 | 1.80 | Neutral |

| | | |
|---|---|---|
| Part A: | | |
| Deionized pigskin gelatin (15% solids) | 40.0 | ml |
| Latex copolymer of Example 3 (15% solids) | 5.0 | ml |
| Resorcinol Coupler (See Table IV below) | 0.003 | mole |
| N,N-Diethyl dodecanamide | 2.0 | ml |
| Ethyl acetate | 2.0 | ml |
| Part B: | | |
| N,N-Diethyl-3-methylparaphenylenediamine hydrochloride | 0.57 | g |
| Methanol | 10.0 | ml |
| Latex copolymer of Example 3 | 10.0 | ml |
| Water | 5.0 | ml |
| Nickel sulfate hexahydrate | 1.4 | g |
| Part C: | | |
| 2',4,4-Trimethyl-1-phenyl-3-pyrazolidone | 0.2 | g |
| Methanol | 5.0 | ml |
| Part D: | | |
| Bis(vinylsulfonylmethyl) ether (3% solids) | 10.0 | ml |
| Surfactant of Example 1 | 2.0 | ml |
| Silver bromoiodide emulsion - green sensitized 54 mgAg$^+$/ml | 10.0 | ml |

EXAMPLE 8

Coating compositions which varied only in the configuration of the linking group (—CONH— and —NHCO—) of the resorcinol coupler were prepared as follows:

TABLE III

| Resorcinol Coupler | $D_{max}$ | Image Hue |
|---|---|---|
| RC-28 | 1.97 | Neutral |
| RC-31 | 1.58 | Neutral |
| RC-33 | 1.68 | Neutral |
| RC-34 | 1.96 | Neutral |
| RC-40 | 1.94 | Neutral |
| RC-52 | 1.52 | Neutral |
| RC-65 | 1.47 | Purple-Black |

Part A was prepared by dissolving the coupler in the coupler solvents and adding it to the gelatin-latex mixture. The mixture was milled in a colloidal mill. Part B was prepared in the order listed and added to Part A. Part C was prepared and added to the dispersion of Parts A and B. The composition was adjusted to pH 4.0 with 50% citric acid and then Part D was added. The resulting composition was coated onto polyethylene coated paper having a gel subbing layer. Analyzed silver coverage of the dried element was 5 mg/dm$^2$.

The dried elements were exposed through a 0.3 density increment step tablet on an EG & G Mark VI Sensitometer at a setting of 10$^{-4}$ second.

The exposed coatings were processed in three ways:
(1) Thirty second activation at 23° C. in 1% sodium hydroxide, 0.1% potassium bromide, 1% benzyl alcohol, and 0.5% 2-(2-aminoethylamino)ethanol; two minutes fix in the fix solution of Example 2; five-minute water wash.
(2) Thirty second activation as in 1; two-minute fix as in 1; two minutes in methanol; five-minute water wash.
(3) Thirty second activation as in 1; one-minute acid stop bath; two minutes in bleach-fix solution A described in Example 1; one-minute water wash; fifteen seconds reactivation in the activator of 1; five-minute water wash.

Process 1 produced a silver plus dye image.
process 2 produced a silver image (no dye).
Process 3 produced a dye image (no silver).
Densities obtained were as shown in following Table IV:

TABLE IV

| Resorcinol Coupler | (Process 1) Silver + Dye Max.Density | (Process 2) Silver Max.Density | (Process 3) Dye Max.Density | Silver + Dye Hue | Dye Hue |
|---|---|---|---|---|---|
| RC-24 | 1.67 | 0.98 | 1.32 | neutral | neutral |
| RC-61 | 1.72 | 1.44* | 1.50 | neutral | blue-black |

*This value is so high for silver image alone that it suggests that Process 2 may have been ineffective in removing all the dye image from the sample.

It should be noted that the linking configuration results in little difference in total density of silver plus dye image of each example and no difference in hue of the silver plus dye image (Process 1). However, oxidative removal of the silver by Process 3 has caused a shift to blue-black in hue of the dye image. It is seen that the total of the density readings from Process 2 and Process 3 are greater than the silver plus dye totals from Process 1. A possible explanation may be that some change in the dye structure or form occurs during the oxidation (bleach-fix) step causing a shift in hue and a change either in dye quantity or in extinction coefficient.

EXAMPLE 9

Coating compositions were prepared having the following composition:

| Part A: | | |
|---|---|---|
| Deionized pigskin gelatin (15% solids) | 40.0 | ml |
| Latex copolymer of 90 mol % n-butyl acrylate and 10 mol % 2-acrylamido-2-methylpropane sulfonic acid (15% solids) | 5.0 | ml |
| Resorcinol Coupler (See Table V, below) | 35 × 10$^{-3}$ | mol |
| 2',4,4-Trimethyl-1-phenyl-3-pyrazolidone | 0.2 | g |
| N,N-Diethyldodecanamide | 2.0 | g |
| Part B: | | |
| Latex copolymer (as above) | 10.0 | ml |
| Ascorbic acid (2% solid) | 0.5 | ml |
| Ethanol | 7.0 | ml |
| N,N-Diethyl-3-methyl-para-phenylenediamine hydrochloride | 0.57 | g |
| Water | 5.0 | ml |
| Nickel sulfate hexahydrate | 1.4 | g |
| Part C: | | |
| Bis(vinylsulfonylmethyl) ether (12% solids) | 15.0 | ml |
| Sodium salt of an alkarylsulfonate (Triton X 200, Trademark) | 0.2 | g |
| Propionic acid | 0.015 | g |
| Silver bromide emulsion - green sensitized-54 mg Ag$^+$/ml | 10.0 | ml |

Part A was prepared by dissolving the coupler and the electron transfer agent in the coupler solvent and adding it to the gelatin-latex mixture. This mixture was milled in a colloid mill.

Part B was prepared in the order listed and added to Part A. This mixture was then adjusted to pH 4.0 with a solution of 50% citric acid.

Part C was added to the mixture, stirred and the composition was coated on a polyethylene-coated paper support having a gel subbing layer. Analyzed silver coverage was approximately 5 mg/dm$^2$.

Portions of the dried elements were exposed through a 0.3 density increment step tableton an E G & G Mark VI Sensitometer at a setting of 10$^{-4}$ second.

The exposed elements were processed in two ways:
(1) Thirty second activation at 23° C. in 1% sodium hydroxide, 0.1% potassium bromide, 1% benzyl alcohol and 0.5% 2-(aminoethylamino)ethanol; two minutes fix in the fix solution of Example 2; five minute water wash.
(2) Thirty second activation as in 1; two minute fix as in 1; two minutes in methanol; five minute water wash.

Process 1 produced a neutral hued silver and dye image.

Process 2 produced a silver image with the dye removed.

Densities obtained were as follows:

TABLE V

| Resorcinol Coupler | Process 1 Silver + Dye Max.Density | Process 2 Silver Max.Density |
|---|---|---|
| RC-24 | 1.50 | 0.82 |
| RC-67 | 1.38 | 0.84 |
| RC-70 | 1.43 | 0.81 |
| RC-71 | 1.45 | 0.78 |
| RC-72 | 1.41 | 0.75 |

This invention has been described with reference to elements containing a color developing agent incorporated therein. Such elements are particularly suitable for rapid processing with simple solutions. However, it will be appreciated that the color developing agent can be omitted from the element and an image developed in the element by treatment with a conventional color developer bath which incorporates in it the color developing agent. The following example illustrates the preparation of such an element and its use to provide a black-and-white image.

EXAMPLE 10

The following coating composition was prepared:

| Part A: | | |
|---|---|---|
| Resorcinol Coupler RC-31 | 0.8 | g |
| Diethyl lauramide | 3.0 | ml |
| Ethyl acetate | 3.0 | ml |
| Latex copolymer of Example 1 (16.5% solids) | 5.0 | ml |
| Deionized pigskin gelatin (12% solids) | 15.0 | ml |
| Water | 10.0 | ml |
| Surfactant of Example 1 (10% solids) | 2.0 | ml |
| Part B: | | |
| Gelatin (as in Part A) | 5.0 | ml |
| 2',4,4-Trimethyl-1-phenyl-3-pyazolidone | 0.25 | g |
| Methyl alcohol | 5.0 | ml |
| Latex copolymer (as in Part A) | 10.0 | ml |
| Bis(vinylsulfonylmethyl) ether (2% solids) | 5.0 | ml |
| Part C: | | |
| Silver bromoiodide emulsion (172 mgAg$^+$/ml) | 9.2 | ml |

Part A was prepared and milled in a colloid mill and then added to Part B. Next Part C was added to the mixture and the resultant composition was coated onto a gel subbed polyethylene terephthalate film support. Analyzed silver coverage of the dried coating was 21 mg/dm$^2$. A portion of the element was exposed as in Example 1 and processed as follows:

Color development in a color developing solution containing 4-amino-3-methyl-N-ethyl-N-β-(methanesulfonamidoethyl)aniline sulfate hydrate color developing agent for 11.5 minutes, followed by:

| Stop | 5.5 minutes |
|---|---|
| Harden | 4 minutes |
| Wash | 3 minutes |
| Bleach | 6 minutes |
| Wash | 4 minutes |
| Fix | 7 minutes |
| Wash | 4 minutes |
| Stabilize | 2 minutes |

After processing, a neutral dye image was obtained having a maximum transmission density of 0.86 and a minimum density of 0.06. The retained silver in the element was less than 2 mg/dm$^2$.

This invention has been described with reference to elements in which a non-diffusible resorcinol coupler is incorporated in the element. However, it will be appreciated that resorcinol couplers having a sufficient diffusibility can be incorporated in a color developer solution employed to process silver halide photographic material. To accomplish this, the resorcinol coupler should be capable of diffusing into the element when incorporated in an alkaline solution such as a color developer bath. The following example illustrates the use of such a compound.

EXAMPLE 11

A photosensitive coating containing 8 mg/dm$^2$ of silver halide in 32 mg/dm$^2$ of gelatin was applied onto a polyethylene terephthalate film support and overcoated with 108 mg/dm² of gelatin containing a hardening agent.

Strips of this film were given sensitometric exposures and processed at 68° C. by

| | |
|---|---|
| Development in a black-and-white developer | 3 minutes |
| Wash | 1 minute |
| Fix | 5 minutes |
| Wash | 5 minutes |
| Rehalogenizing bleach | 5 minutes |
| Wash | 10 minutes |
| Rinse (distilled water) | 30 seconds |
| Redevelopment in a solution containing 3.1 g/l 4-amino-3-methyl-N,N-diethylaniline hydrochloride and 1.56 g/l of Resorcinol Coupler RC-35 | 10 minutes |
| Wash | 5 minutes |
| Fix | 5 minutes |
| Wash | 5 minutes |
| Bleach | 5 minutes |
| Wash | 5 miutes |
| Fix | 5 minutes |
| Wash | 10 minutes |
| Rinse 30 seconds | |

A spectrophotometric curve of the resulting dye image showed absorption across the entire visible region of the spectrum.

This invention has been described with certain preferred embodiments thereof, but it should be understood that variations and modifications can be effected within the spirit and scope of the invention.

We claim:

1. A black-and-white photographic element comprising a support bearing an image-forming layer comprising a photographic silver halide emulsion, a color developing agent or a precursor of a color developing agent and an image-forming nondiffusible resorcinol coupler having the structure:

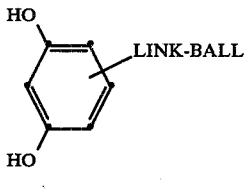

where
LINK represents —NHCO—, —COHN—, —NHCONH—, —NHSO₂—, or —COO—; and
BALL represents phenyl, naphthyl, substituted phenyl, substituted naphthyl, alkyl, of 3 to 20 carbon atoms or a heterocyclic group containing 5 to 10 nuclear atoms,
the element yielding upon exposure and development to a density of between 0.3 and 2.0, a spectrophotometric curve in which the density of any 10 nm interval in the range of 420 to 650 nm does not depart by more than ten percent from the mean density over that range.

2. A photographic element of claim 1, wherein the color developing agent precursor is a Schiff base.

3. A photographic element of claim 1, wherein the color developing agent precursor is a Schiff base of a p-phenylenediamine.

4. A photographic element of claim 1, wherein the color developing agent is present in its protonated form.

5. A photographic element of claim 4, wherein the color developing agent is a p-phenylenediamine.

6. A photographic element of claim 1, further comprising an electron transfer agent.

7. A photographic element of claim 6, wherein the electron transfer agent is a 3-pyrazolidone.

8. A photographic element of claim 1, further comprising a polymeric latex.

9. A black-and-white photographic element comprising a support bearing an image-forming layer of a photographic silver halide emulsion, a color developing agent or a precursor of a color developing agent and an image-forming non-diffusible resorcinol coupler represented by the formula:

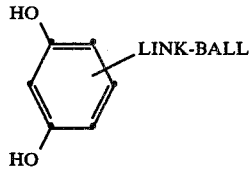

where:
LINK represents —NHCO— or —COO—; and
BALL represents an alkyl group of 3 to 20 carbon atoms, a phenyl group, or a phenyl group substituted with alkyl of 1 to 20 carbon atoms or with alkoxy of 1 to 20 carbon atoms,
the element yielding upon exposure and development to a density of between 0.3 and 2.0, a spectrophotometric curve in which the density of any 10 nm interval in the range 420 to 650 nm does not depart by more than ten percent from the mean density over that range.

10. A photographic element of claim 9, wherein the color developing agent precursor is a Schiff base of a p-phenylenediamine.

11. A photographic element of claim 9 wherein the color developing agent is a p-phenylenediamine present in its protonated form.

12. A photographic element of claim 9, further comprising a 3-pyrazolidone electron transfer agent.

13. A photographic element of claim 9, further comprising a polymeric latex.

14. A photographic element of claim 9, wherein —LINK—BALL is ortho to each hydroxy group.

15. A photographic element of claim 14 wherein LINK is —NHCO— and BALL is an alkyl group of 8 to 20 carbon atoms or a phenyl group substituted with alkyl of 8 to 20 carbon atoms or with alkoxy of 8 to 20 carbon atoms.

16. A photographic element of claim 14, wherein LINK is —COO— and BALL is an alkyl group of 8 to 20 carbon atoms or a phenyl group substituted with alkyl of 8 to 20 carbon atoms or with alkoxy of 8 to 20 carbon atoms.

17. A photographic element of claim 9, wherein the non-diffusible resorcinol coupler is selected from the group consisting of:
2',6'-dihydroxy-2-methoxybenzanilide,
2',6'-dihydroxy-4-n-octylbenzanilide,
n-octyl-2,6-dihydroxybenzoate and
n-decyl-2,6-dihydroxybenzoate.

18. A photographic element of claim 17, further comprising a pyrazolidone electron transfer agent.

19. A photographic element of claim 15, wherein the color developing agent precursor is the Schiff base, p-(benzylideneamino-4-methoxy-3-sulfonic acid)-N,N-diethyl-3-methyl aniline.

20. A photographic element of claim 19, further comprising a latex.

21. A photographic element of claim 18, wherein the color developing agent is N,N-diethyl-3-methyl-p-phenylene diamine hydrochloride.

22. A black-and-white photographic element comprising a support bearing an image-forming layer of:
a silver halide emulsion;
an image-forming non-diffusible resorcinol coupler selected from the group consisting of
2'6'-dihydroxy-2-methoxybenzanilide,
2'6'-dihydroxy-4n-octylbenzanilide,
n-octyl-2,6-dihydroxybenzoate and
n-decyl-2,6-dihydroxybenzoate;
a Schiff base of a p-phenylenediamine color developing agent; and
a 3-pyrazolidone electron transfer agent; the element yielding upon exposure and development to a density of between 0.3 and 2.0, a spectrophotometric curve in which the density of any 10 nm interval in the range 420 to 650 nm does not depart by more than ten percent from the mean over that range.

23. A black-and-white photographic element comprising a support bearing an image-forming layer of:
a silver halide emulsion;
an image-forming non-diffusible resorcinol coupler selected from the group consisting of
2'6'-dihydroxy-2-methoxybenzanilide,
2'6'-dihydroxy-4-n-octylbenzanilide,
n-octyl-2,6-dihydroxybenzoate and
n-decyl-2,6-dihydroxybenzoate;
a p-phenylenediamine color developing agent;
and a 3-pyrazolidone electron transfer agent; the element yielding upon exposure and development to a density of between 0.3 and 2.0, a spectrophotometric curve in which the density of any 10 nm interval in the range 420 to 650 nm does not depart by more than ten percent from the mean density over that range.

24. A process of providing a black-and-white image in an imagewise exposed photographic element comprising a support bearing an image-forming layer comprising a photographic silver halide emulsion, a color developing agent or a precursor of a color developing agent and an image-forming nondiffusible resorcinol coupler having the structure:

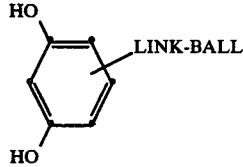

where:
LINK represents —NHCO—, —CONH—, —NH-CONH—, —NHSO₂—, or —COO—; and
BALL represents phenyl, naphthyl, substituted phenyl, substituted naphthyl, alkyl of 3 to 20 carbon atoms or a heterocyclic group containing 5 to 10 nuclear atoms,
the element yielding upon exposure and development to a density of between 0.3 and 2.0, a spectrophotometric curve in which the density of any 10 nm interval in the range of 420 to 650 nm does not depart by more than ten percent from the mean density over that range,
the process comprising activating the element by contacting it with an aqueous alkaline solution to develop a neutral density image as a function of exposure.

25. The process of claim 24 further comprising the step of fixing the developed element to remove undeveloped silver halide.

26. The process of claim 25 further comprising the step of treating the developed element, prior to fixing, with an acid bath to terminate development.

27. The process of claim 24 further comprising the step of bleach-fixing the developed element to remove developed silver and undeveloped silver halide.

28. The process of claim 24 further comprising the step of treating the developed element with a monobath containing a non-dye-forming silver halide developing agent and a fixing agent.

29. The process of claim 27 further comprising the step of treating the bleach-fixed element with an aqueous alkaline solution.

30. A process of providing a black-and-white image in an imagewise exposed photographic element comprising a support bearing an image-forming layer of a photographic silver halide emulsion, a color developing agent or a precursor of a color developing agent and an image-forming non-diffusible resorcinol coupler represented by the formula:

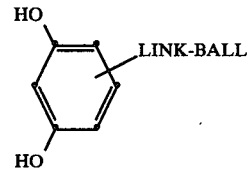

where
LINK represents —NHCO— or —COO— and
BALL represents an alkyl group of 3 to 20 carbon atoms, a phenyl group or a phenyl group substituted with alkyl of 1 to 20 carbon atoms or with alkoxy of 1 to 20 carbon atoms,
the element yielding upon exposure and development to a density of between 0.3 and 2.0, a spectrophotometric curve in which the density of any 10 nm interval in the range of 420 to 650 nm does not depart by more than ten percent from the mean density over that range,
the process comprising the steps of:
activating the element by contacting it with an aqueous alkaline activator solution to develop a neutral density image as a function of exposure; and fixing the developed element to remove undeveloped silver halide.

31. The process of claim 30 wherein the aqueous alkaline activator solution has a pH of 11 to 14 and comprises an inorganic base, a solvent for the developing agent and an antifoggant.

32. The process of claim 31 wherein the aqueous alkaline activator solution further comprises an amine development accelerator.

33. The process of claim 31 wherein the aqueous alkaline activator solution further comprises a cobalt III complex.

34. A process of providing a black-and-white image in an imagewise exposed photographic element comprising a support bearing an image-forming layer of a photographic silver halide emulsion, a color developing agent or a precursor of a color developing agent and an image-forming non-diffusible resorcinol coupler represented by the formula:

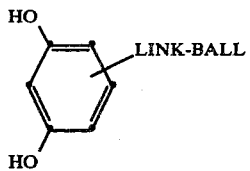

where
LINK represents —NHCO—OR—COO—and
BALL represents an alkyl group of 3 to 20 carbon atoms, a phenyl group or a phenyl group substituted with alkyl of 1 to 20 carbon atoms or with alkoxy of 1 to 20 carbon atoms, the element yielding upon exposure and development to a density of between 0.3 and 2.0, a spectrophotometric curve in which the density of any 10 nm interval in the range of 420 to 650 nm does not depart by more than ten percent from the mean density over that range, the process comprising the steps of:
  activating the element by contacting it with an aqueous alkaline activator solution to develop a neutral density image as a function of exposure;
  terminating development by treating the developed element with an acid bath;
  bleach-fixing the developed element to remove developed silver and undeveloped silver halide; and treating the bleach-fixed element with an aqueous alkaline solution.

35. The process of claim 34 wherein the aqueous alkaline activator solution has a pH of 11 to 14 and comprises an inorganic base, a solvent for the color developing agent and an antifoggant.

36. The process of claim 35 wherein the aqueous alkaline activator solution further comprises an amine development accelerator.

37. The process of claim 35 wherein the aqueous alkaline activator solution further comprises a cobalt III complex.

* * * * *